United States Patent
Kaneko et al.

(10) Patent No.: US 6,828,155 B1
(45) Date of Patent: Dec. 7, 2004

(54) METHOD FOR EVALUATING LIPID A ANALOG-CONTAINING INJECTIONS

(75) Inventors: Kazuhiro Kaneko, Ibaraki (JP); Tomohiro Watanabe, Ibaraki (JP); Yasuyuki Asai, Aichi (JP); Yoshihisa Sano, Ibaraki (JP); Kiyomi Kikuchi, Ibaraki (JP); Ikuo Kushida, Ibaraki (JP); Kazuhide Ashizawa, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/786,060

(22) PCT Filed: Aug. 26, 1999

(86) PCT No.: PCT/JP99/04615

§ 371 (c)(1),
(2), (4) Date: Mar. 1, 2001

(87) PCT Pub. No.: WO00/13029

PCT Pub. Date: Mar. 9, 2000

(30) Foreign Application Priority Data

Sep. 1, 1998 (JP) .......................................... 10-246862

(51) Int. Cl.[7] ............................................ G01N 33/00
(52) U.S. Cl. ............................................ 436/71
(58) Field of Search ............................................ 436/71

(56) References Cited

FOREIGN PATENT DOCUMENTS

| JP | A62129292 | 6/1987 |
| JP | A62252795 | 11/1987 |
| JP | A4198192 | 7/1992 |
| JP | 05194470 A | 8/1993 |
| WO | 9639411 | 12/1996 |

OTHER PUBLICATIONS

Haruhiko Takada and Shozo Kotani, Protein Nucleic acid and Enzyme, vol. 31(4), p. 361 (1986) with abstract; described in specification at p. 1, lines 10–11.

Yuji Ogawa et al., Metabolism, vol. 26(5), p. 415(1989) with abstract; described in specification at p. 1, line 13.

C. Galanos et al., Eur. J. Biochem., vol. 31, pp. 230–233(1972).

R.B. Ramsey et al., Blood, vol. 56(2), pp. 307–310(1980).

J. Dijkstra et al., J. Immunol., vol. 138, pp. 2663–2670(1987).

*Primary Examiner*—Jill Warden
*Assistant Examiner*—Monique T. Cole
(74) *Attorney, Agent, or Firm*—Birch, Stewart, Kolasch & Birch, LLP

(57) ABSTRACT

The present invention provides an evaluation method and preparation process of injection containing a lipid A analog. Specifically, it provides, in an injection preparation containing a lipid A analog or a pharmacologically acceptable salt thereof, forecasting and evaluating methods of the pharmacokinetics of the lipid A analog, and quality evaluating method and preparation process of the injection, which each comprises measuring membrane fluidity and/or circular dichroism.

22 Claims, 4 Drawing Sheets

METHOD FOR EVALUATING LIPID A ANALOG-CONTAINING INJECTIONS

This application is the national phase under 35 U.S.C. §371 of PCT International Application No. PCT/JP99/04615 which has an International filing date of Aug. 26, 1999, which designated the United States of America.

Evaluation method and preparation process of injection containing a lipid A analog

FIELD OF THE INVENTION

The present invention relates to a method for forecasting and evaluating the pharmacokinetic parameter of an injection containing lipid A analog, a quality evaluating method of the injection for ensuring the injection to have constant pharmacokinetic parameter, and a preparation process of the injection.

PRIOR ART

Lipid A is the main moiety causing activities of lipopolysaccharide (hereinafter referred to as LPS), has various biological activities such as macrophage stimulation, antitumor effect and pyrogenicity (for example, Haruhiko Takada and Shozo Kotani, *Protein, Nucleic Acid and Enzyme*, 31(4), 361 (1986)).

Various lipid A analogs have recently been synthesized and examined for their biological activities (Yuji Ogawa et al., *Metabolism* 26(5), 415 (1989)). Most of the Lipid A analogs having the glycolipid structure are sparingly soluble in water, so that it is difficult to prepare an injection with lipid A analogs.

In order to prepare an injection and to obtain a highly transparent aqueous solution, the addition of triethylamine, bovine serum albumin, lipids, or the like (Y. B. Kim, et al, *Eur. J. Biochem.* 31, 230 (1972) and R. B. Ramsey, et al, *Blood*, 56, 307 (1980), J. Dijkstra, et al, *J. Immunol.*, 138, 2663 (1987)) and use of basic amino acids or polyamines (JP-A 4-198192) as a solubilizing agent have been reported.

On the other hand, as a method of dispersing a lipid such as lecithin or the like in water to form aggregates of liposomes or the like, known is a method to add a lipid to a buffer having a pH around neutrality, followed by heating and sonication.

The inventors have prepared an injection preparation having a high transparency, which contains aggregates having a diameter not greater than 30 nm, prepared by dissolving the lipid A analog or a pharmacologically acceptable salt thereof produced according to the methods disclosed in JP-A 5-194470 and WO96/39411 in an alkaline aqueous solution and then adding a buffer thereto.

Administration of this injection preparation to the living body of a rat or a beagle is however accompanied with the problem that the blood level of a lipid A analog shows a large variation, depending on the difference in the raw material medicament or preparation lot. This occurs because the state of the aggregates of the medicament (lipid) in the solution of the injection preparation is not uniform.

It is the common practice to evaluate the state of the aggregates of a lipid in a solution from the appearance observed through an electron microscope, particle size distribution measured by a laser diffraction particle size distribution measuring apparatus or consideration based on the physical properties such as critical micelle concentration or surface tension.

Not so many reports have however been proposed on circular dichroism spectroscopy and/or membrane fluidity evaluation method employed as an evaluation method of the invention.

In circular dichroism spectroscopy (which will hereinafter be abbreviated as "CD spectroscopy"), measurement is carried out reflecting the difference in the refractive index and absorbance of an optically active substance between those relative to left hand circular polarized light and those relative to right hand circular polarized light. This method is frequently employed for the conformation analysis of peptides or proteins or optical activity analysis of low-molecular compounds, but it has hardly been employed for the analysis of lipid-related substances. Reported are only the case wherein a dynamic change of a lipid in a liposome membrane depending on temperature was investigated by the analysis of variations in a CD spectrum (JP-A 62-252795); the case wherein CD spectroscopy is useful for evaluation of the characteristics of lipid particles in water, is an evaluation method markedly simple in operation and permits measurement of a dynamic state change in the membrane at a diluted concentration (N. Nakashima et al, CHEM. LET., 1503, 10 (1985)); and a case wherein CD spectroscopy is employed as one of the evaluation methods of the correlation between the characteristics of aggregates in various formulations of Prostaglandin E1 in liposome and elution characteristics (Sharon M. K. et al, Biochim. Biophys. Acta, 1327, 97 (1997)).

As a method for evaluating membrane fluidity (softness of membrane), known are fluorescence probe method, electron spin resonance (ESR) method and nuclear magnetic resonance (NMR) method (Robert B Gennith; Biomembrane, p146 (1992), published by Springer Verlag, Tokyo). Among them, the fluorescence probe method is a method for evaluating membrane fluidity having a bimolecular membrane structure of phospholipid. In this method, the state of the membrane in the vicinity of a fluorescent substance is observed by mixing a fluorescence probe such as diphenylhexatriene (which will hereinafter be abbreviated as "DPH") in the membrane of lipid and then, measuring the polarity of fluorescence emitted upon exposure to polarized incident light. There is a report of the application of this method to a lipid A analog (Braudenburg K, et al., Biochim. Biophys. Acta, 225, 775 (1984)). The fluorescence probe method makes it possible to calculate fluorescence polarity (P: ranging from 0 to 0.5) and/or fluorescence anisotropy (r: ranging from 0 to 0.4) and/or order parameter (S: ranging from 0 to 1.0) by measuring the vertical polarizing component and horizontal polarizing component of fluorescence emitted from a lipid sample (Hiroshi Terada, Tetsuro Yoshimura; Liposome in Life Science (1992), published by Springer Verlag, Tokyo). Herein, as the order parameter (S) approaches 0, the membrane fluidity becomes larger. As it approaches 1, on the other hand, the membrane fluidity becomes smaller.

No report has however been published yet on the definite forecasting or evaluation of the pharmacokinetic parameter of a lipid A analog based on the correlation between the measuring and evaluating results of the aggregate condition of the medicament in a solution and the pharmacokinetic parameter. In addition, a report has been made neither on a process for producing an injection preparation wherein the pharmacokinetic parameter of a lipid A analog has been controlled nor a quality assurance method for ensuring the injection preparation to have predetermined pharmacokinetic parameter, each from the viewpoints of the state of the aggregates of the medicament (lipid) in a solution.

It is possible to prepare an injection preparation containing aggregates having a diameter not greater than 30 nm by dissolving a lipid A analog or pharmacologically acceptable salt thereof in an aqueous alkaline solution and then adding a buffer thereto. In the resulting injection preparation, the lipid A analog or pharmacologically acceptable salt thereof constitutes endoplasmic reticulum with lipid biomolecular membrane or micelle structure. In other words, an injection of a lipid A analog which has high transparency in the form of an aqueous solution, a preferred pH range as an injection and good stability can be prepared by the above-described process.

The injection preparation thus prepared is however accompanied with the problem that when it is administered to a rat or beagle, the blood level varies largely from one lot to another of a raw material medicament or the preparation. This owes to that the existing state of a lipid A analog in a solution, that is, the aggregate structure in the form of endoplasmic reticulum of lipid biomolecular membrane or micelle having a diameter not greater than 30 nm differs with the lot of the raw material medicament or injection preparation. There is accordingly a strong demand for the development of a practically usable injection of a lipid A analog, that is, an injection having uniform pharmacokinetic parameter, which is typified by the blood level, without being influenced by the difference among the lots of a raw material medicament or injection preparation; and a forecasting and evaluating method of the pharmacokinetic parameter of the injection.

DISCLOSURE OF THE INVENTION

With the foregoing in view, the present inventors have carried out an extensive investigation to search for an injection containing a lipid A analog, having high transparency and having good stability and in addition, exhibiting constant uniform pharmacokinetic parameter free from the influence of variations of a raw material medicament or injection preparation among lots; and forecasting and evaluating method of the pharmacokinetic parameter of the injection. As a result, it has been found that the object can be attained by the below-described constitutions, leading to the completion of the present invention.

In one aspect of the present invention, there is provided a forecasting method of the pharmacokinetic parameter of a lipid A analog in an injection preparation containing the lipid A analog or pharmacologically acceptable salt thereof, which comprises measuring membrane fluidity and/or circular dichroism in a solution.

In another aspect of the invention, there is also provided an evaluation method of the pharmacokinetic parameter of a lipid A analog in an injection preparation containing the lipid A analog or a pharmacologically acceptable salt thereof, which comprises measuring membrane fluidity and/or circular dichroism in a solution.

In a further aspect of the present invention, there is also provided a quality assurance method of an injection preparation containing a lipid A analog or a pharmacologically acceptable salt thereof, which comprises measuring and evaluating membrane fluidity and/or circular dichroism in a solution, and ensuring the lipid A analog to exhibit constant pharmacokinetic parameter in vivo.

The forecasting method of the pharmacokinetic parameter according to the present invention can be employed for the evaluation of an injection preparation, quality evaluation for obtaining an injection preparation exhibiting constant pharmacokinetic parameter or preparation of the injection preparation.

According to the present invention, an injection preparation which is transparent and is ensured to have stable pharmacokinetic parameter is available using a lipid A analog or a pharmacologically acceptable salt (which will hereinafter be called "lipid A analog", collectively). This is an object of the present invention. In addition, the present invention provides a forecasting and evaluating method of the pharmacokinetic parameter of an injection preparation containing the lipid A analog by measuring the membrane fluidity and/or circular dichroism; and also provides a quality evaluating method of an injection preparation containing a lipid A analog, which ensures the lipid A analog to exhibit constant pharmacokinetic parameter. This is another object of the present invention.

The lipid A analog of the present invention is represented by the following chemical structure, and can be produced by the process disclosed in, for example, JP-A 5-194470 or WO96/39411.

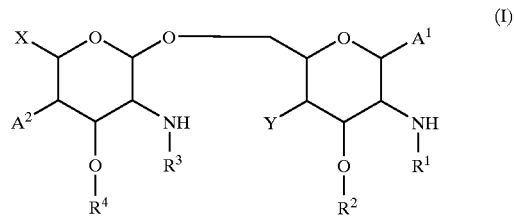

(I)

wherein at least one of $R^1$, $R^2$, $R^3$ and $R^4$ is

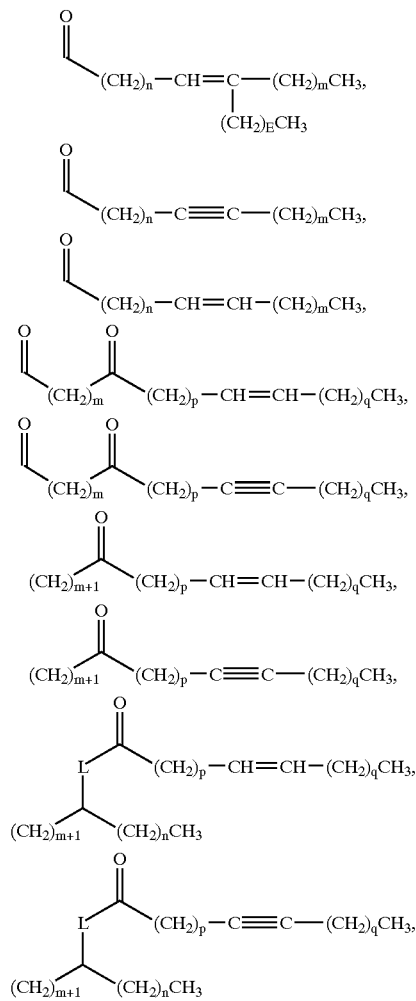

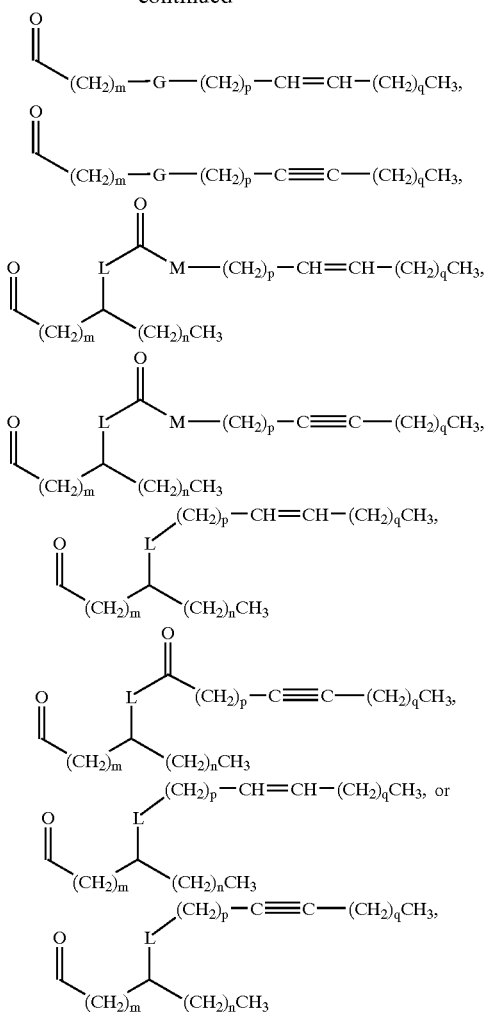

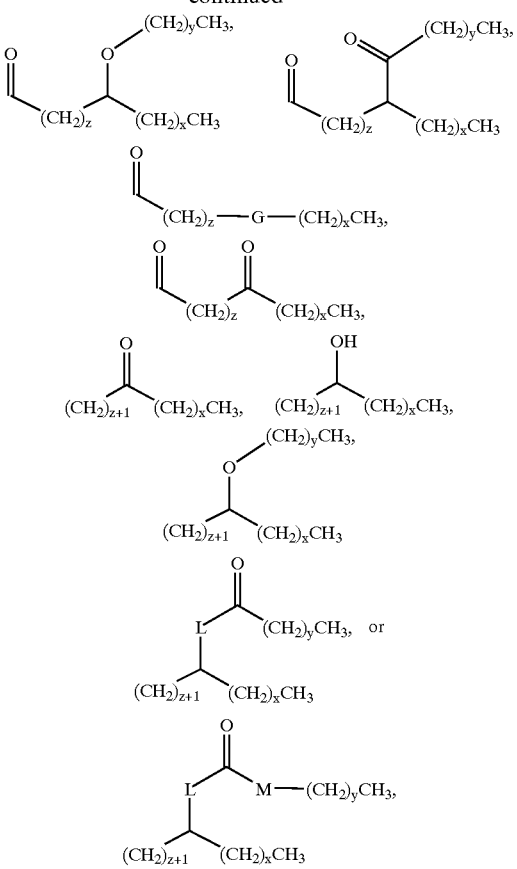

wherein each L is O, N or C; each M is O or N; each x independently is an integer of 0 to 14; each y independently is an integer of 0 to 14; each z independently is an integer of 0 to 14; each G independently is N, O, S, SO or SO$_2$, wherein each L is O, N or C; each M is O or N; each E independently is an integer of 0 to 14; each G independently is N, O, S, SO or SO$_2$; each m independently is an integer of 0 to 14; each n independently is an integer of 0 to 14; each p independently is an integer of 0 to 10; each q independently is an integer of 0 to 10, the rest of R$^1$, R$^2$, R$^3$ and R$^4$ are, independently of one another, $A^1$ and $A^2$ are, independently of one another, H, OH, OCH$_3$,

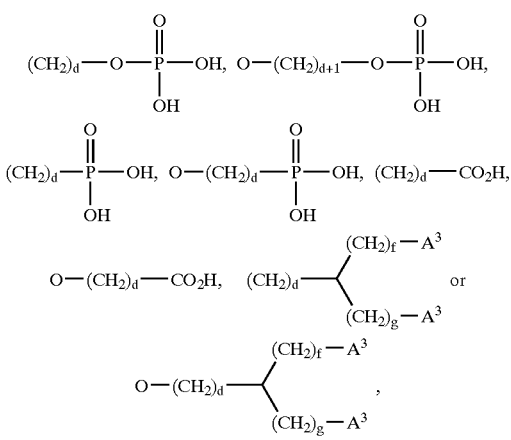

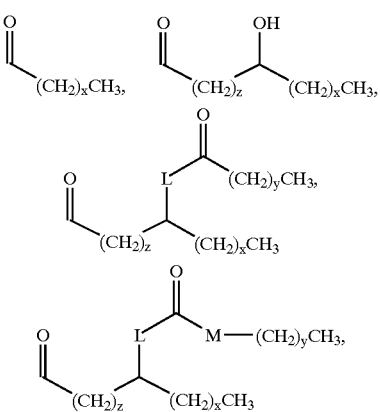

wherein each d independently is an integer of 0 to 5; each f independently is an integer of 0 to 5; each g independently is an integer of 0 to 5; each A$^3$ independently is

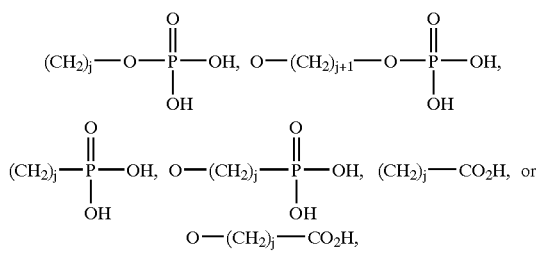

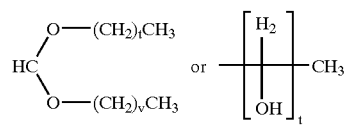

wherein each j independently is an integer of 0 to 14, X is H, $(CH_2)_tCH_3$, $(CH_2)_tOH$, $(CH_2)_tO(CH_2)_vCH_3$, $(CH_2)_tOPO(OH)_2$, $(CH_2)_t-CH=CH-(CH_2)_vCH_3$, $(CH_2)_t-O-R^5$,

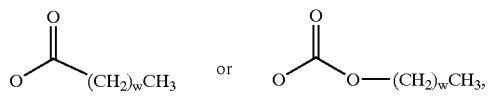

wherein t and v, are independently of one another, an integer of 0 to 14; $R^5$ is any of the above definitions of $R^1$ to $R^4$, Y is H, OH, $O(CH_2)_wCH_3$, a halogen atom,

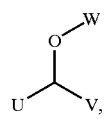

wherein w is an integer of 0 to 14.

(II)

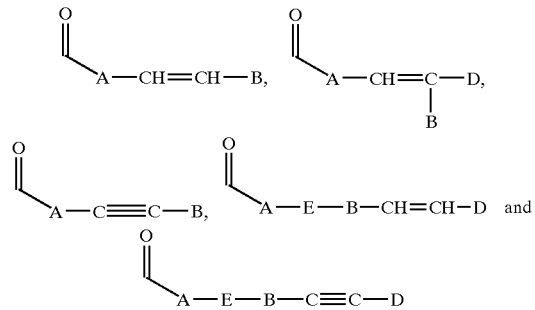

wherein $R^1$ is a group selected from the groups consisting of

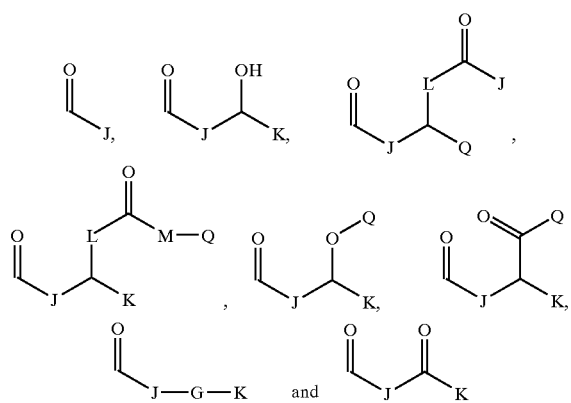

wherein J, K and Q are each a linear or branched alkyl group of 1 to 15 carbon atoms; L is O, $NH_2$ or $CH_2$; M is O or NH; G is NH, O, S, SO or $SO_2$, $R^2$ is a linear or branched alkyl group of 5 to 15 carbon atoms, $R^3$ is a group selected from the groups consisting of

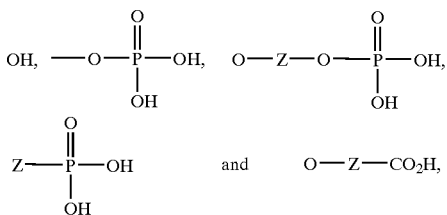

wherein E is N, O, S, SO or $SO_2$; A, B and D are each a linear or branched alkyl group of 1 to 15 carbon atoms, $R^4$ is a group selected from the groups consisting of a linear or branched alkyl group of 4 to 20 carbon atoms and wherein U and V are each a linear or branched alkyl group of 2 to 15 carbon atoms; W is a hydrogen atom or a linear or branched alkyl group of 1 to 5 carbon atoms, $R^5$ is a group selected from the groups consisting of a hydrogen atom, J', —J'—OH, —J'—O—K', —J'—O—K'—OH and —J'—O—PO(OH)$_2$, wherein J' and K' are each a linear or branched alkyl group of 1 to 5 carbon atoms, $R^6$ is a group selected from the groups consisting of a hydroxyl group, a halogen atom, an alkoxy group of 1 to 5 carbon atoms, and an acyloxy group of 1 to 5 carbon atoms, $A^1$ and $A^2$ are, independently of one another, a group selected from the groups consisting of wherein Z is a linear or branched alkyl group of 1 to 10 carbon atoms.

Preferred examples of the lipid A analog for use in the present invention include 6-O-[2-deoxy-6-O-methyl-4-O-phosphono-3-O-[(R)-3-Z-dodec-5-enoyloxydecyl]-2-[3-oxo-tetradecanoylamido]-b-O-phosphono-a-D-glucopyranose]tetrasodium, a-D-glucopyranose, 3-O-decyl-2-deoxy-6-O-[2-deoxy-3-O-(3-methoxydecyl)-6-O-methyl-2-[(1-oxo-11-octadecenyl)amino]-4-O-phosphono-b-D-glucopyranosyl]-2-[(1,3-dioxotetradecyl)amino]-, 1-(dihydrogenphosphate), disodium[6(2Z, 3R)]; and a-D- glucopyranose, 3-O-decyl-2-deoxy-6-O-[2-deoxy-3-O-(3-methoxydecyl)-6-O-methyl-2-[(1-oxo-11-octadecenyl)amino]-4-O-phosphono-b-D-glucopyranosyl]-2-((1,3-dioxotetradecyl)amino]-, 1-(dihydrogenphosphate), tetrasodium[6(2Z, 3R)]. These compounds are represented by the following chemical structural formulae (III) and (IV).

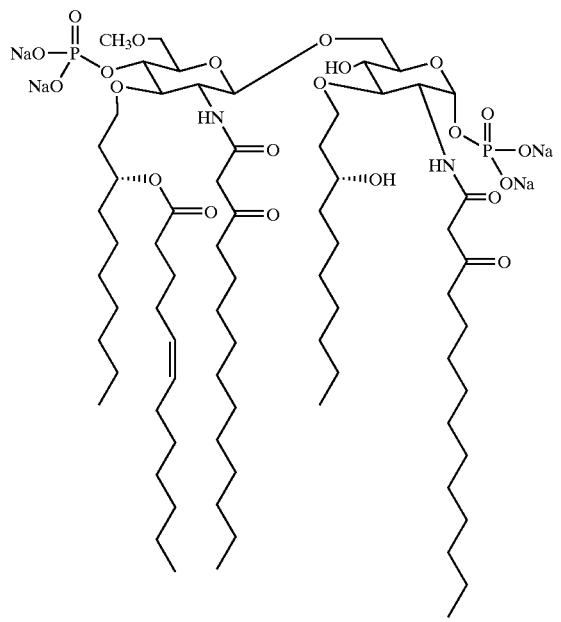

(III)

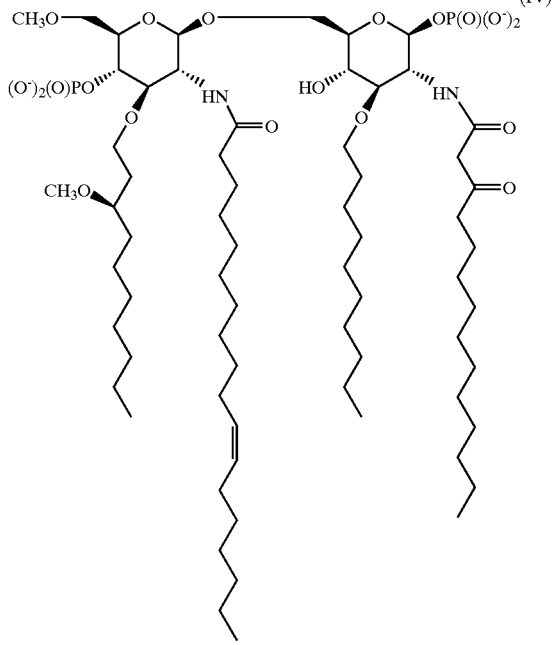

(IV)

It is known that the blood level of liposome of phospholipid is influenced largely when it is introduced into a net system such as liver via a scavenger receptor. As a result of study on the mechanism of a scavenger receptor which recognizes and scavenges an anionic high molecule such as liposome, it is also known that membrane fluidity (softness of membrane), surface charge and particle diameter play important roles in the recognition of the scavenger receptor (Hiroshi Terada, Tetsuro Yoshimura; Liposome in Life Science, p326 (1992), published by Springer Verlag, Tokyo).

No example of evaluating physicochemical properties of the membrane of a preparation containing a lipid A analog has so far been proposed from the viewpoint of pharmacokinetic control.

The present invention has revealed that in a step for preparing an injection preparation which contains aggregates having a diameter not greater than 30 nm by dissolving a lipid A analog in an alkaline solution and then adding a buffer to the resulting solution, a pharmacokinetic profile of the injection containing a lipid-A analog can be controlled by measuring and evaluating its membrane fluidity and circular dichroism.

The membrane fluidity of the particles in an injection preparation using DPH has a close correlation with a blood level profile. Upon administration of the injection preparation, a preparation having larger membrane fluidity (a preparation having softer membrane) disappears more slowly from the blood larger AUC), while a preparation having smaller membrane fluidity (a preparation having harder membrane) disappears more rapidly from the blood (smaller AUC). This is because after administration of a lipid-A-containing injection, membrane fluidity affects the pharmacokinetic parameter of the medicament. The larger the membrane fluidity, the lipid A does not tend to be trapped easily by a scavenger receptor and is therefore not taken in a phagocyte such as liver cells readily, retarding the disappearance of lipid A from the circulating blood. The present invention has also revealed that there is a correlation between the CD spectrum change and variations in the pharmacokinetic parameter.

The present invention makes it possible to prepare an injection preparation containing a lipid-A analog ensured to have good pharmacokinetic parameter by utilizing, for the measurement of membrane fluidity and/or circular dichroism, the fact that membrane fluidity and/or circular dichroism in the solution of the injection differs definitely between a formulation of a low disappearing rate and a formulation of a high disappearing rate from the blood. The present invention also makes it possible to provide a forecasting or evaluating method of the pharmacokinetic parameter of an injection preparation containing a lipid-A analog by measuring membrane fluidity and/or circular dichroism; and a quality evaluating method for ensuring the injection to have constant pharmacokinetic parameter.

In the present invention, a highly-transparent injection preparation which has controlled pharmacokinetic parameter and contains aggregates having a diameter not greater than 30 nm can be prepared by dissolving a lipid A analog in an aqueous alkaline solution, adding thereto a buffer and measuring membrane fluidity and/or circular dichroism in the resulting solution. In the present invention, the membrane fluidity of an injection preparation is measured by the fluorescence probe method. This is a method for evaluating membrane fluidity of a bimolecular membrane structure of a phospholipid. Described specifically, the state of the membrane in the vicinity of a fluorescent substance is observed by mixing a fluorescence probe in the membrane of a lipid and measuring the polarity of fluorescence emitted upon exposure to polarized incident light. In the present invention, any one or more than one parameter selected from fluorescence polarity (P: ranging from 0 to 0.5), fluorescence anisotropy (r: ranging from 0 to 0.4) and order parameter (S: ranging from 0 to 1.0) may be used for evaluation of membrane fluidity. As a fluorescence probe to be used, any one capable of emitting stable fluorescence can be employed. Examples include diphenylhexatriene (DPH), carboxyfluorescein, calcein, Nile Red, pyrene and perylene.

For example, as the order parameter (S) approaches 0, the membrane fluidity is larger, while it approaches 1.0, the membrane fluidity is smaller. The order parameter (S) of the lipid A analog represented by the formula (III) or (IV) is usually 0.5 to 0.7, preferably 0.1 to 0.6, more preferably 0.1 to 0.5.

The circular dichroism spectroscopy (CD spectroscopy) of an injection preparation employed in the present invention is useful as a method for controlling or forecasting the pharmacokinetic parameter of a lipid A analog. It is preferred to evaluate the CD spectrum of each of a number of injection preparations and select the wavelength at which a large difference in CD intensity can be recognized. In the CD spectroscopy of the lipid A analog represented by the formula (III) or (IV), wavelength measured is usually 260 to 320 mm, preferably 270 to 310 mm, more preferably 280 to 300 mm.

As the alkaline aqueous solution in the present invention, the hydroxide of an alkali metal such as sodium hydroxide and potassium hydroxide, preferably sodium hydroxide may be used. The concentration thereof generally ranges from 0.0001M to 0.1M, preferably from 0.0005M to 0.01M and more preferably from 0.001 M to 0.01 M.

In the present invention, after an alkaline aqueous solution is added to a lipid A analog, the temperature of the mixture may be elevated. The elevated temperature must be higher than the phase transition temperature of the lipid A analog or a pharmacologically acceptable salt thereof, but has no more limitation. The elevated temperature generally ranges from 30° C. to 60° C., preferably 45° C. to 55° C. The stirring time generally ranges from 10 minutes to 3 hours. Stirring may be carried out with a conventional apparatus. When a lipid A analog is dissolved in a heated alkaline aqueous solution, a lipid A analog may be added to an alkaline aqueous solution which is heated in advance. Alternatively, after a lipid A analog is added to an alkaline aqueous solution, the mixture may be heated. In the present invention, the purpose of elevating the temperature is to accelerate hydration of lipid A analogs to improve dispersibility by elevating the temperature to the phase transition temperature of lipid A analogs or higher, to thereby obtain a transparent solution by stirring for a shortened period of time.

The lipid A analog represented by the formula (IV) however may be heated or stirred at room temperature for 10 minutes to 1.5 hours.

Examples of the component of the buffer for use in the present invention include phosphates, Tris(hydroxymethyl)aminomethane, citrates, glycine and the like. The concentration of the buffer generally ranges from 1 mM to 20 mM. The final pH value of the aqueous solution of the lipid A analog is preferably 4 to 9, more preferably 6 to 8, still more preferably 6.8 to 7.8. The final pH value may be adjusted by adding a solution of sodium hydroxide, hydrochloric acid, or the like after the addition of the buffer.

If necessary, addition of saccharides and/or amino acids to the buffer may give a more preferable result. In this case, saccharides and/or amino acids to be added may be either one, or two or more kinds thereof. Examples of the saccharide include milk sugar (lactose), sorbitol, glucose, trehalose, mannitol, dextran, and the like. Examples of the amino acid include neutral amino acids such as glycine, acidic amino acids such as aspartic acid, and basic amino acids such as arginine.

In the present invention, the resulting lipid A analog aqueous solution may be freeze-dried by a conventional method to obtain a freeze-dried preparation. Namely, lipid A or an analog thereof is dissolved in an alkaline aqueous solution, further stirred at an elevated temperature if necessary, followed by addition of a buffer to adjust pH of the mixture. After sterilizing filtration, the mixture is filled into a vial or the like, followed by freeze-drying to give a freeze-dried preparation.

When a preparation for injection according to the present invention is administered in the form of aqueous solution, the osmotic pressure ratio of the preparation is preferably adjusted to a value suitable for administrating to humans, generally around 1.

One example of each of the measuring methods of membrane fluidity and circular dichroism (CD spectroscopy) of an injection preparation and the evaluation method of the pharmacokinetic parameter in a rat administered with the preparation will next be described.

It will be evaluated using as a parameter fluorescence polarity (P) and/or fluorescence anisotropy (r) and/or order parameter (S) in accordance with the fluorescence probe method.

First, a solution having a concentration of 0.5 to 0.6 mg/ml is prepared as an injection preparation containing a lipid-A analog (a freeze-dried preparation in a 1.5 to 1.6 mg/vial is prepared by adding 3 ml of distilled water). Then, 4 µl of a fluorescence probe solution obtained by dissolving 1.5 mg of DPH in 10 ml of THF is added, followed by sufficient mixing. The resulting mixture is allowed to stand at 50° C. for 1 hour. After cooling to room temperature, P and/or r of the reaction mixture is measured by a fluorescent spectrophotometer. The measuring conditions of a fluorescent spectrophotometer "Model F-450" (trade name; product of Hitachi Ltd.) are as follows: excited wavelength of 360 nm, luminous wavelength of 428 mm, applied voltage of 700V, measuring temperature of 25° C. and slit width of 5 nm. The order parameter (S) is calculated based on the equation: $S=(r/0.398)^{1/2}$.

It can be judged that membrane fluidity is larger (the membrane is softer) at S closer to 0 and it is smaller (the membrane is harder) at S closer to 1. Measuring method of circular dichroism (CD spectroscopy) of the preparation A solution having a concentration of 0.5 to 0.6 mg/ml is prepared as an injection containing a lipid A analog (a freeze-dried preparation in a 1.5 to 1.6 mg/vial is prepared by adding 3 ml of distilled water). The CD intensity of this preparation is evaluated by "Spectropolarimeter J720WI" (trade name; product of JASCO Corporation). Measurement is conducted under the conditions of wavelength of 200 to 500 nm (280 nm when fixed wavelength is employed), measuring temperature at room temperature, cell length of 1 cm, scanning speed of 20 nm/min and integration of 5 times.

Evaluation method of pharmacokinetic parameter in a rat administered with an injection preparation The pharmacokinetic parameter profile of the preparation is judged using as a parameter an area under the curve available from the time-dependent curve of the blood level of medicament (this area will hereinafter be abbreviated as "AUC").

First, as an injection preparation containing a lipid A analog, a solution having a concentration of 0.6 mg/ml is prepared by adding distilled water for injection. The resulting solution is administered (0.6 mg/Kg) to a male SD rat in a dose of 1 ml/Kg from its femoral vein. In addition to the blood collection prior to administration, the blood is collected 2, 5, 15, 30, 60 and 120 minutes after administration, each in an amount of 0.25 ml. Each of the bloods thus collected is centrifuged, whereby the plasma is obtained. From the plasma, the lipid A analog is extracted by liquid-liquid extraction, followed by labeling with fluorescence by using an ADAM reagent (product of Funakoshi Co., Ltd.). After solid layer extraction, the concentration of the lipid A analog contained in the plasma is measured using high performance liquid chromatography in accordance with the fluorescence detection method. The AUC is calculated from a change in the blood level from 0 to 120 minutes.

According to the present invention, it is possible to provide an injection preparation containing a lipid A analog as that having high transparency and stably controlled pharmacokinetic parameter. Also a forecasting method and evaluating method of the pharmacokinetic parameter of an injection preparation and a quality assurance method of an injection preparation containing a lipid A analog, which ensures the preparation to have constant pharmacokinetic parameter can be provided. The following are the advantage examples of the present invention.

TEST 1

Figure 1:
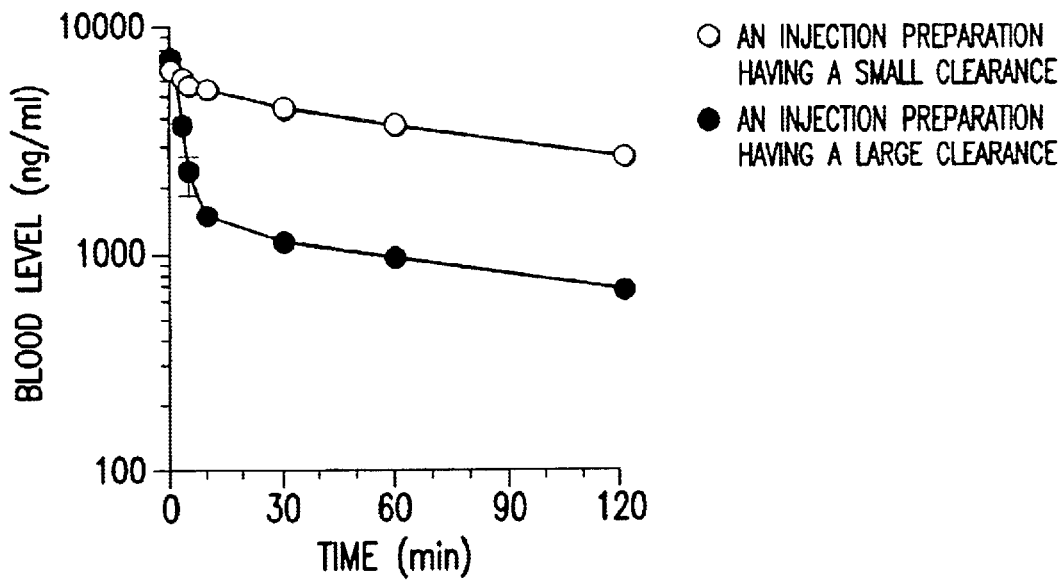
FIG. 1 is a graph showing a change in the blood level of a rat administered (0.6 mg/kg) with an injection preparation containing the lipid A analog represented by the formula (IV).

Evaluation of the membrane fluidity and circular dichroism of the preparations different in the profile of pharmacokinetic parameter (AUC), according to the present invention 1) An injection preparation having a small clearance was prepared in the following manner. In a 50 ml glass beaker, 32.47 mg of the lipid A analog represented by the formula (IV) was weighed. After the addition of 7.5 mL of 0.01M NaOH, the resulting mixture was stirred by a stirrer bar (2 cm long) at room temperature for 60 minutes. To the reaction mixture was added 25 mL of a lactose.phosphate buffer (an aqueous solution obtained by dissolving in 25 mL of purified water 500 mg of lactose.monohydrate, 2.25 mg of $Na_2HPO_4.7H_2O$ and 1.75 mg of $NaH_2PO_4.H_2O$). After stirring for 5 minutes by a stirrer bar, the whole amount of the mixture was transferred to a 50 mL measuring flask. Distilled water for injection was then added to adjust the total amount to 50 mL.

2) An injection preparation having a large clearance was prepared in the following manner. In a 50 ml glass beaker, 32.97 mg of the lipid A analog represented by the formula (IV) was weighed. After the addition of 0.25 mL of 0.01M NaOH and 7.25 mL of distilled water for injection, the resulting mixture was stirred by a stirrer bar (2 cm long) at room temperature for 60 minutes. To the reaction mixture was added 25 mL of a lactose.phosphate buffer (an aqueous solution obtained by dissolving in 25 mL of purified water 500 mg of lactose monohydrate, 2.25 mg of $Na_2HPO_4.7H_2O$ and 1.75 mg of $NaH_2PO_4.H_2O$). After stirring for 5 minutes by a stirrer bar, the whole amount of the mixture was transferred to a 50 mL measuring flask and then mixed with 7.45 mL of 0.1M NaOH. By the further addition of 0.01M NaOH, pH of the mixture was adjusted to 7.4. Distilled water for injection was then added to increase the total amount to 50 mL.

These two injection preparations thus prepared, that is, a formulation 1) having a small clearance and a formulation 2) having a large clearance, were evaluated for a correlation between AUC wand each of membrane fluidity and circular dichroism.

As illustrated in FIG. 1, a change in the blood level of a rat administered with an injection preparation containing a lipid A analog differed largely between an injection preparation of a small clearance and that of a large clearance. The order parameter (S) as an indicator of membrane fluidity was 0.499 in the case of an injection preparation having a small clearance, while that in the case of an injection preparation having a large clearance was 0.624, indicating that there was a significant difference between them.

Figure 2:
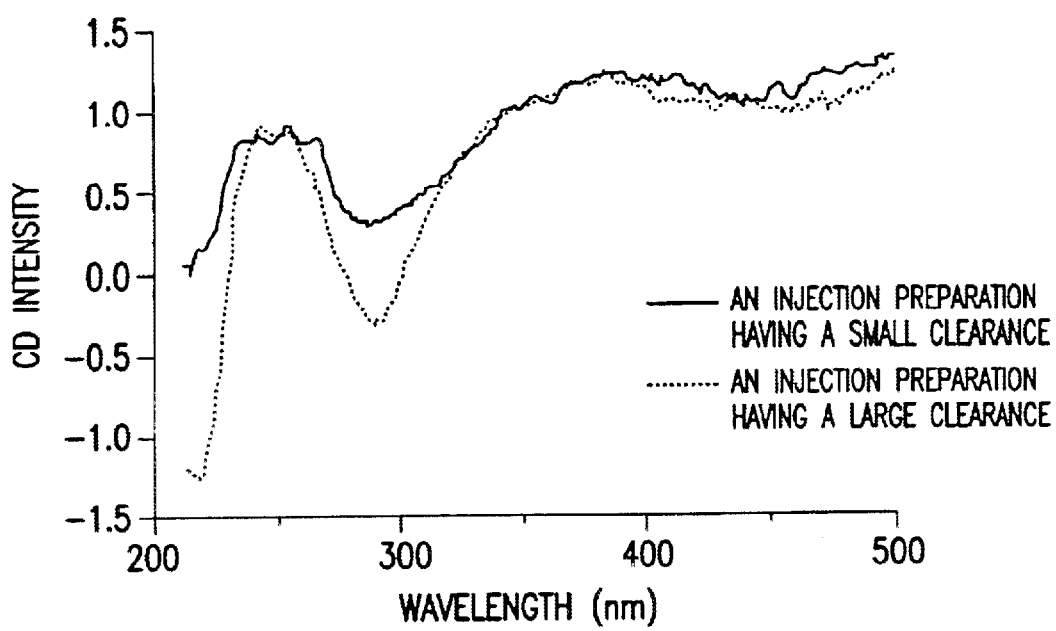
FIG. 2 is a graph showing a CD spectrum (spectrum as evaluated by circular dichroism spectroscopy) of an injection preparation containing the lipid A analog represented by the formula (IV).

In CD intensity as measured by circular dichroism (CD spectroscopy), as shown in FIG. 2, a clear difference was recognized between them at wavelength of 280 nm. The above-described findings show clearly that evaluation of membrane fluidity and/or circular dichroism is useful for evaluating a change in the pharmacokinetic parameter of the lipid-A-analog-containing injection preparation according to the present invention.

TEST 2

Figure 3:
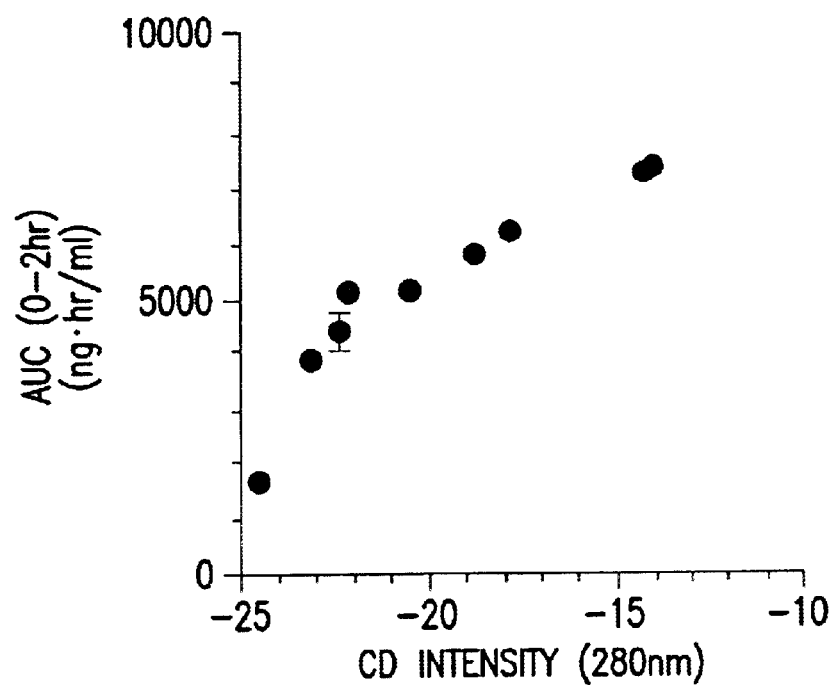
FIG. 3 is a graph showing a correlation between CD intensity and AUC (upon administration to a rat) of an injection preparation containing the lipid A analog represented by the formula (IV).
Figure 4:
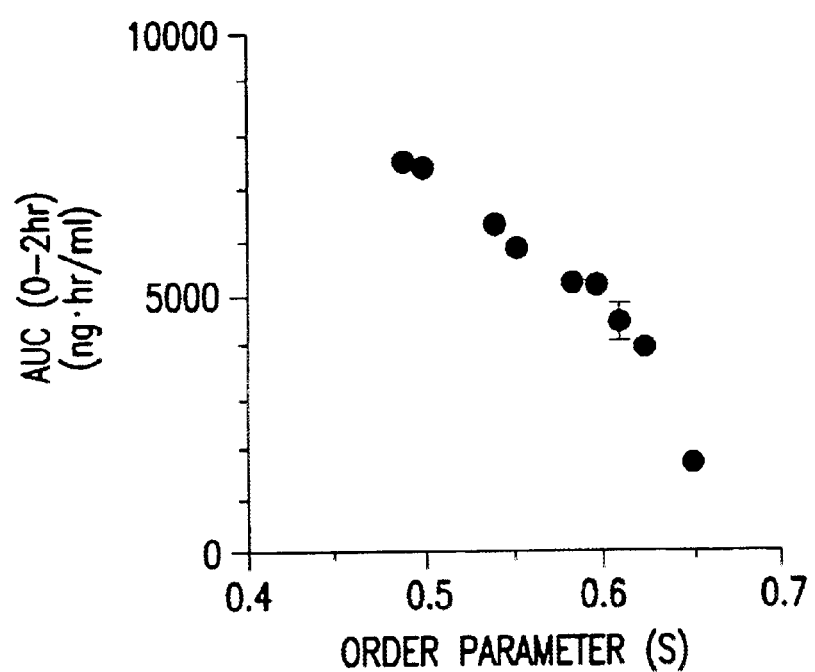
FIG. 4 is a graph showing a correlation between order parameter (S) and AUC (upon administration to a rat) of an injection preparation containing the lipid A analog represented by the formula (IV).
Figure 5:
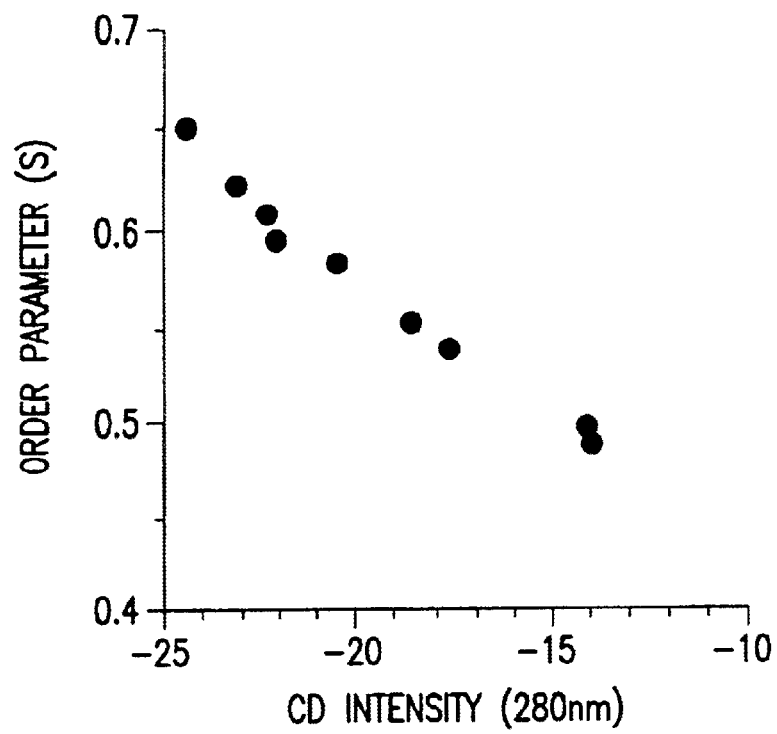
FIG. 5 is a graph showing a correlation between the CD intensity and order parameter (S) of an injection preparation containing the lipid A analog represented by the formula (IV).

Measurement and evaluation of membrane fluidity and/or circular dichroism of the injection preparation according to the present invention and a correlation between AUC and membrane fluidity or circular dichroism Ten lots of an injection preparation containing the lipid A analog represented by the formula (IV) were prepared and a correlation between CD intensity (at wavelength of 280 nm) and/or order parameter (S) and AUC of a rat intravenously administered with the preparation was evaluated. As a result, as shown in FIG. 3, a good, positive correlation was recognized between AUC of the rat and CD intensity. The preparation having a greater CD intensity exhibited greater AUC. As shown in FIG. 4, a good, negative correlation was, on the other hand, recognized between AUC of the rat and order parameter (S). The smaller the order parameter (S) (as it approached 0), the greater AUC. As shown in FIG. 5, a good, negative correlation was recognized between the CD intensity (at wavelength of 280 nm) and order parameter (S)

of the injection preparation. The greater the CD intensity, the smaller the order parameter (S) (it approached 0).

Figure 6:
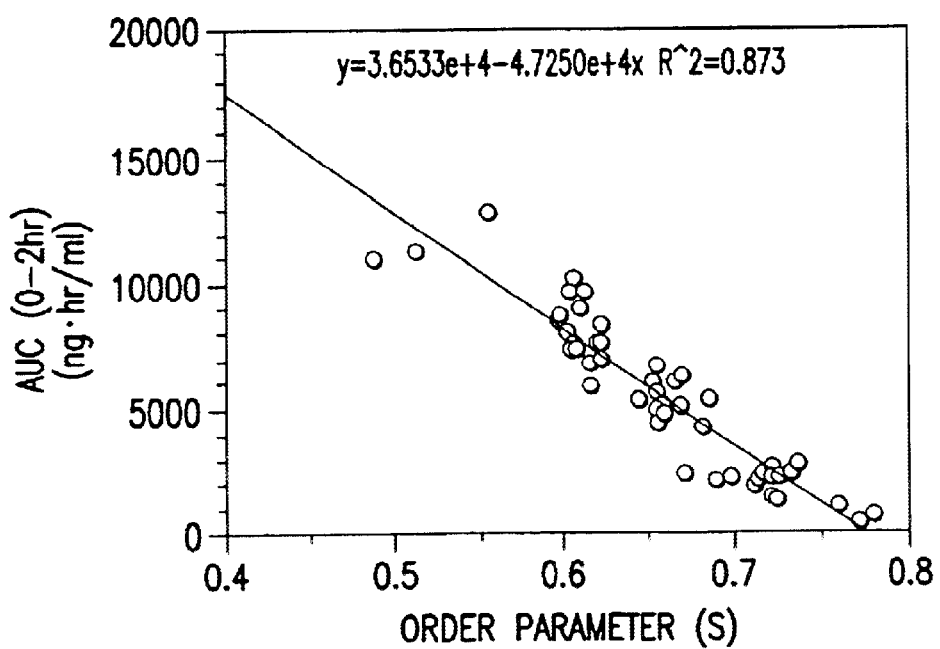
FIG. 6 is a graph showing a correlation between the order parameter (S) and AUC (upon administration to rat) of an injection preparation containing the lipid A analog represented by the formula (III).
Figure 7:
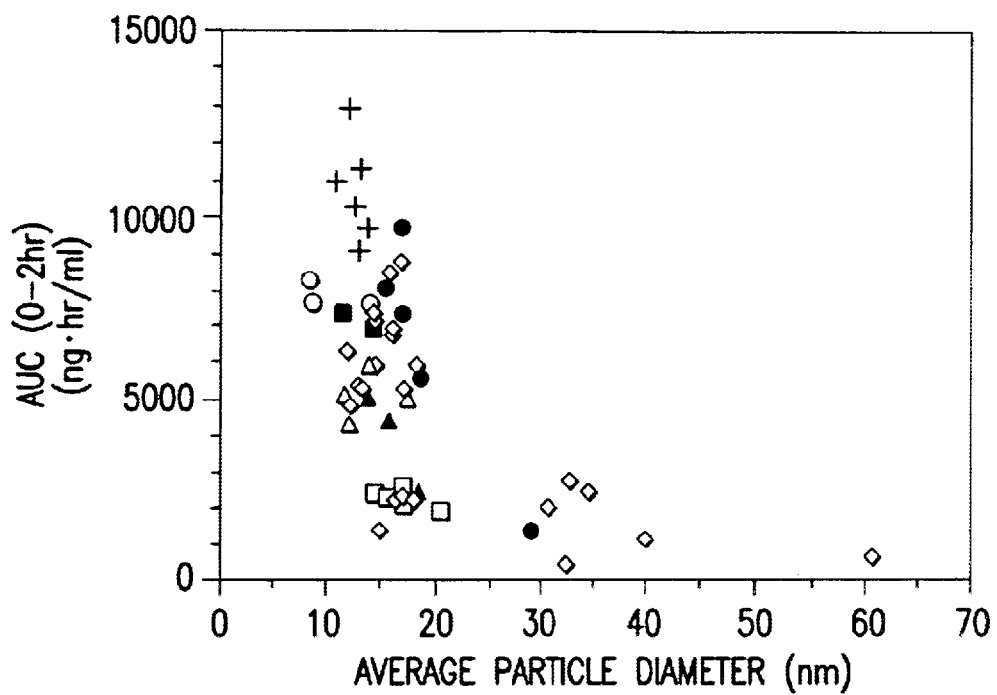
FIG. 7 is a graph showing a correlation between the particle size and AUC (upon administration to a rat) of an injection preparation containing the lipid A analog represented by the formula (III).

Concerning an injection preparation containing the lipid A analog represented by the formula (III), ten lots were prepared and evaluated. As a result, a negative correlation was recognized between the AUC of a rat and order parameter (S) as shown in FIG. 6 and its correlation coefficient was 0.873. Concerning the correlation between AUC of a rat and the average particle diameter of the injection preparation, AUC showed large variations at an average particle diameter ranging from 10 to 20 mm and therefore, no definite correlation was recognized (FIG. 7) between them. Accordingly, evaluation using an average particle size was insufficient for forecasting and evaluation of pharmacokinetic parameter.

Thus, a good correlation of a pharmacokinetic parameter profile (AUC) with evaluation of membrane fluidity and/or circular dichroism of the injection preparation according to the present invention has been proved. It is evident that use of membrane fluidity (order parameter (S)) and circular dichroism (CD) is fully effective for forecasting and evaluating the pharmacokinetic parameter of an injection preparation containing a lipid A analog. In addition, it becomes possible to prepare an injection preparation having ensured pharmacokinetic parameter by evaluating the state of aggregates in the solution based on membrane fluidity and/or circular dichroism. In other words, AUC can be presumed by measuring the order parameter (S) and/or circular dichroism (CD) of an injection preparation containing lipid A analog. Accordingly, the present invention can therefore be used industrially and useful.

EXAMPLES

The present invention will hereinafter be described more specifically by referring to Examples. However, the present invention is not limited by them.

Figure 8:
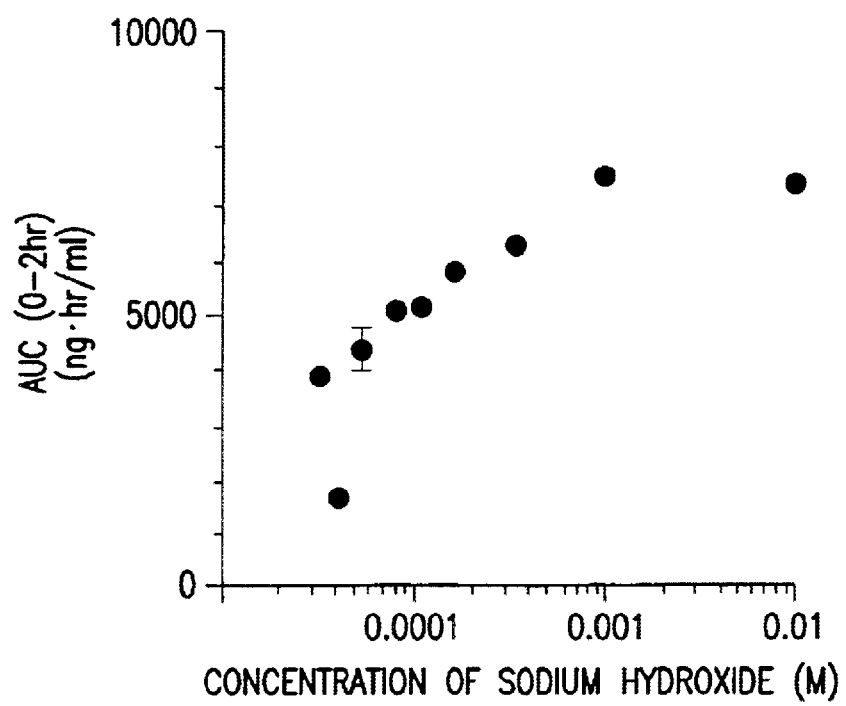
FIG. 8 is a graph showing a correlation between the concentration of sodium hydroxide and AUC (upon administration to a rat) in a dissolution step of an injection preparation containing the lipid A analog represented by the formula (IV).

In Examples 1 to 10 which will be described below, shown are aqueous injections prepared by changing the concentration of sodium hydroxide (NaOH) used for dissolving therein a lipid A analog represented by the formula (IV). Table 1 shows the CD intensity and the order parameter (S) of each injection preparation and AUC upon administration to a rat. Further, in FIG. 8 is shown a correlation between the concentration of sodium hydroxide (NaOH) used in the above-described dissolving step and AUC. The greater the concentration of sodium hydroxide (NaOH), the greater each of AUC and order parameter (S). At 0.001 to 0.1M, AUC and order parameter (S) reached a plateau. This means that the ensured and/or forecast optimum concentration of sodium hydroxide (NaOH) used in the dissolving step of an injection preparation containing the lipid A analog represented by the formula (IV) was 0.001 to 0.01M.

Example 1

In a 50 mL glass beaker, 32.47 mg of a lipid A analog of the formula (IV) was weighed and 7.5 mL of 0.01M NaOH was added to it. The resulting mixture was stirred by a stir bar of 2 cm long at room temperature for 60 minutes (the concentration of sodium hydroxide (NaOH) employed in the dissolving step: 0.01M). To the reaction mixture was added 25 mL of a lactose.phosphate buffer (25 mL of an aqueous solution having 500 mg of lactose monohydrate, 2.25 mg of $Na_2HPO_4.7H_2O$ and 1.75 mg of $NaH_2PO_4.H_2O$ dissolved therein). After stirring by a stirrer for 5 minutes, the total amount of the reaction mixture was transferred to a 50 mL measuring flask. Distilled water for injection was then added to adjust the total amount to 50 mL. The solution at this time had a pH of 7.39.

Example 2

In a 50 mL glass beaker, 2.23 mg of the lipid A analog of the formula (IV) was weighed and 0.75 mL of 0.01M NaOH and 6.75 mL of distilled water for injection were added to it. The resulting mixture was stirred by a stir bar of 2 cm long at room temperature for 60 minutes (the concentration of sodium hydroxide (NaOH) employed in the dissolving step: 0.01M×1/10). To the reaction mixture was added 25 mL of a lactose.phosphate buffer (a 25 mL aqueous solution having 500 mg of lactose monohydrate, 2.25 mg of $Na_2HPO_4.7H_2O$ and 1.75 mg of $NaH_2PO_4.H_2O$ dissolved therein). After stirring by a stirrer for 5 minutes, the total amount of the reaction mixture was transferred to a 50 mL measuring flask. In the measuring flask, 6.75 mL of 0.01M NaOH was charged and they were mixed. Distilled water for injection was then added to adjust the total amount to 50 mL. The solution at this time had a pH of 7.41.

Example 3

In a 50 mL glass beaker, 32.13 mg of the lipid A analog of the formula (IV) was weighed and 0.25 mL of 0.01 N NaOH and 7.25 mL of distilled water for injection were added to it. The resulting mixture was stirred by a stir bar of 2 cm long at room temperature for 60 minutes (the concentration of sodium hydroxide (NaOH) employed in the dissolving step: 0.01M×1/30). To the reaction mixture was added 25mL of a lactose.phosphate buffer (a 25mL aqueous solution having 500 mg of lactose monohydrate, 2.25 mg of $Na_2HPO_4.7H_2O$ and 1.75 mg of $NaH_2PO_4.H_2O$ dissolved therein). After stirring by a stirrer for 5 minutes, the total amount of the reaction mixture was transferred to a 50 mL measuring flask. In the measuring flask, 7.25 mL of 0.01M NaOH was charged further and they were mixed. Distilled water for injection was then added to adjust the total amount to 50 mL. The solution at this time had a pH of 7.42.

Example 4

In a 50 mL glass beaker, 32.16 mg of the lipid A analog of the formula (IV) was weighed and 0.125 mL of 0.01M NaOH and 7.375 mL of distilled water for injection were added to it. The resulting mixture was stirred by a stirbar of 2 cm long at room temperature for 60 minutes (the concentration of sodium hydroxide (NaOH) employed in the dissolving step: 0.01M×1/60). To the reaction mixture was added 25 mL of a lactose.phosphate buffer (a 25 mL aqueous solution having 500 mg of lactose monohydrate, 2.25 mg of $Na_2HPO_4.7H_2O$ and 1.75 mg of $NaH_2PO_4.H_2O$ dissolved therein). After stirring by a stirrer for 5 minutes, the total amount of the reaction mixture was transferred to a 50 mL measuring flask. In the measuring flask, 7.375 mL of 0.01M NaOH was charged further and they were mixed. Distilled water for injection was then added to adjust the total amount to 50 mL. The solution at this time had a pH of 7.30.

Example 5

In a 50 mL glass beaker, 32.63 mg of the lipid A analog of the formula (IV) was weighed. A 5.0 mL portion of the mixture of 0.125 mL of 0.01M NaOH and 7.375 mL of distilled water for injection was added, followed by further addition of 2.5 mL of distilled water for injection. The resulting mixture was stirred by a stir bar of 2 cm long at room temperature for 60 minutes (the concentration of sodium hydroxide (NaOH) employed in the dissolving step: 0.01M×1/90). To the reaction mixture was added 25 mL of a lactose.phosphate buffer (a 25 mL aqueous solution having 500 mg of lactose monohydrate, 2.25 mg of $Na_2HPO_4.7H_2O$ and 1.75 mg of $NaH_2PO_4.H_2O$ dissolved therein). After stirring by a stirrer for 5 minutes, the total amount of the reaction mixture was transferred to a 50 mL measuring flask. In the measuring flask, 7.4 mL of 0.01M-NaOH was charged. After mixing, 0.01M NaOH was added further to adjust the pH of the mixture to 7.4. Distilled water for injection was then added to give the total amount of 50 mL. The solution at this time had a pH of 7.42.

Example 6

In a 50 mL glass beaker, 32.07 mg of the lipid A analog of the formula (IV) was weighed, followed by the addition of a 3.75 mL portion of a solution containing 0.125 mL of 0.01M NaOH and 7.375 mL of distilled water for injection. To the resulting mixture, 3.75 mL of distilled water for injection was added further. The resulting mixture was stirred by a stir bar of 2 cm long at room temperature for 60 minutes (the concentration of sodium hydroxide (NaOH) employed in the dissolving step: 0.01M×1/120). To the reaction mixture was added 25 mL of a lactose.phosphate buffer (a 25 mL aqueous solution having 500 mg of lactose monohydrate, 2.25 mg of $NaHPO_4.7H_2O$ and 1.75 mg of $NaH_2PO_4.H_2O$ dissolved therein). After stirring by a stirrer for 5 minutes, the whole amount of the reaction mixture was transferred to a 50 mL measuring flask. In the measuring flask, 7.4 mL of 0.01N NaOH was further charged and they were mixed. The mixture was adjusted to pH 7.4 by further addition of 0.01M NaOH. Distilled water for injection was then added to give the total amount of 50 mL. The solution at this time had a pH of 7.48.

Example 7

In a 50 mL glass beaker, 32.43 mg of the lipid A analog of the formula (IV) was weighed. A 5.0 ml portion of a solution obtained by mixing 0.125 mL of 0.01M NaOH and 14.875 mL of distilled water for injection was then added, followed by the addition of 2.5 mL of distilled water for injection. The resulting mixture was stirred by a stir bar of 2 cm long at room temperature for 60 minutes (the concentration of sodium hydroxide (NaOH) employed in the dissolving step: 0.01M×1/180). To the reaction mixture was added 25 mL of a lactose.phosphate buffer (a 25 mL aqueous solution having 500 mg of lactose monohydrate, 2.25 mg of $Na_2HPO_4.7H_2O$ and 1.75 mg of $NaH_2PO_4.H_2O$ dissolved therein). After stirring by a stirrer for 5 minutes, the whole amount of the reaction mixture was transferred to a 50 mL measuring flask. In the measuring flask, 7.45 mL of 0.01M-NaOH was further charged and they were mixed. After pH adjustment to 7.4 with 0.01M NaOH, distilled water for injection was added to give the total amount of 50 mL. The solution at this time had a pH of 7.41.

Example 8

In a 50 mL glass beaker, 32.84 mg of the lipid A analog of the formula (IV) was weighed. A 3.75 ml portion of the solution obtained by mixing 0.125 mL of 0.01M NaOH and 14.875 mL of distilled water for injection was then added, followed by the addition of 3.75 mL of distilled water for injection. The resulting mixture was stirred by a stir bar of 2 cm long at room temperature for 60 minutes (the concentration of sodium hydroxide (NaOH) employed in the dissolving step: 0.01M×1/240). To the reaction mixture was added 25 mL of a lactose.phosphate buffer (a 25 mL aqueous solution having 500 mg of lactose monohydrate, 2.25 mg of $Na_2HPO_4.7H_3O$ and 1.75 mg of $NaH_2PO_4.H_2O$ dissolved therein). After stirring by a stirrer for 5 minutes, the whole amount of the reaction mixture was transferred to a 50 mL measuring flask. In the measuring flask, 7.45 mL of 0.01M NaOH was charged and they were mixed. After pH adjustment to 7.4 by the addition of 0.01M-NaOH, distilled water for injection was added to give the total amount of 50 mL. The solution at this time had a pH of 7.41.

Example 9

In a 50 mL glass beaker, 32.35 mg of a lipid A analog of the formula (IV) was weighed. A 0.75 ml portion of the solution obtained by mixing 0.25 mL of 0.01M NaOH and 7.25 mL of distilled water for injection was then added, followed by the addition of 6.75 mL of distilled water for injection. The resulting mixture was stirred by a stir bar of 2 cm long at room temperature for 60 minutes (the concentration of sodium hydroxide (NaOH) employed in the dissolving step: 0.01M×1/350). To the reaction mixture was added 25 mL of a lactose.phosphate buffer (a 25 mL aqueous solution having 500 mg of lactose monohydrate, 2.25 mg of $Na_2HPO_4.7H_2O$ and 1.75 mg of $NaH_2PO_4.H_2O$ dissolved therein). After stirring by a stirrer for 5 minutes, the whole amount of the reaction mixture was transferred to a 50 mL measuring flask. In the measuring flask, 7.45 mL of 0.01M-NaOH was charged and they were mixed. After pH adjustment with 0.01M NaOH to 7.4, distilled water for injection was added to give the total amount of 50 mL. The solution at this time had a pH of 7.41.

Example 10

In a 50 mL glass beaker, 32.97 mg of the lipid A analog of the formula (IV) was weighed. A 0.5 ml portion of a solution obtained by mixing 0.25 mL of 0.01M NaOH and 7.25 mL of distilled water for injection was then added, followed by the addition of 7.0 mL of distilled water for injection. The resulting mixture was stirred by a stir bar of 2 cm long at room temperature for 60 minutes (the concentration of sodium hydroxide (NaOH) employed in the dissolving step: 0.01M×1/450). To the reaction mixture was added 25 mL of a lactose.phosphate buffer (a 25 mL aqueous solution having 500 mg of lactose monohydrate, 2.25 mg of $Na_2HPO_4.7H_2O$ and 1.75 mg of $NaH_2PO_4.H_2O$ dissolved therein). After stirring by a stirrer for 5 minutes, the whole amount of the reaction mixture was transferred to a 50 mL measuring flask. In the measuring flask, 7.45 mL of 0.01M NaOH was charged and they were mixed. After pH adjustment with 0.01M-NaOH to 7.4, distilled water for injection was added to give the total amount of 50 mL. The solution at this time had a pH of 7.43.

TABLE 1

Physicochemical parameter of an injection preparation containing a lipid A analog and AUC (0–2 hr) of a rat administered with the preparation

| Example | Concentration (M) of NaOH in the dissolving step | AUC (0–2 hr) (ng · hr/ml) | CD Intensity | Order parameter (S) |
| --- | --- | --- | --- | --- |
| Ex 1 | 0.01 | 7377 ± 261 | −14.1 | 0.499 |
| Ex 2 | 0.01 × 1/10 | 7465 ± 276 | −13.9 | 0.491 |
| Ex 3 | 0.01 × 1/30 | 6231 ± 318 | −17.7 | 0.540 |
| Ex 4 | 0.01 × 1/60 | 5817 ± 117 | −18.6 | 0.553 |

TABLE 1-continued

Physicochemical parameter of an injection preparation containing a lipid A analog and AUC (0–2 hr) of a rat administered with the preparation

| Example | Concentration (M) of NaOH in the dissolving step | AUC (0–2 hr) (ng · hr/ml) | CD Intensity | Order parameter (S) |
|---|---|---|---|---|
| Ex 5  | 0.01 × 1/90  | 5158 ± 173 | −20.5 | 0.584 |
| Ex 6  | 0.01 × 1/120 | 5078 ± 290 | −22.1 | 0.595 |
| Ex 7  | 0.01 × 1/180 | 4388 ± 358 | −22.3 | 0.608 |
| Ex 8  | 0.01 × 1/240 | 1665 ± 106 | −24.5 | 0.650 |
| Ex 9  | 0.01 × 1/300 | 3858 ± 255 | −23.1 | 0.624 |
| Ex 10 | 0.01 × 1/450 | —          | −21.9 | 0.616 |

AUC: Mean ± S.D.

In Examples 11 to 21 which will be described below, stirring was conducted at room temperature in Examples 11 to 16, while ultrasonic dispersion (at 10° C. or less) was conducted in Examples 17 to 21, each in the dissolving step for the preparation of an injection preparation containing the lipid A analog represented by the formula (III). Since the phase transition temperature of the lipid A analog represented by the formula (III) is about 30° C., sufficient dissolution and dispersion was not available in Examples 11 to 21 and large variations in AUC of the rat administered with the preparation and physicochemical parameters including order parameter (S) were recognized as shown in Table 2.

membrane fluidity (order parameter (S), fluorescence anisotropy r, fluorescence polarity P) are shown in Table 2.

In a glass beaker, 100 mg of the lipid A analog represented by the formula (III) was weighed, followed by the addition of 150 mL of 0.01M NaOH. The resulting mixture was stirred by a stirrer at room temperature. After visual conformation of the disappearance of a gel of the lipid analog A represented by the formula (III), the glass beaker was subjected to ultrasonic exposure at a temperature maintained at 10° C. or less in a bath type sonicator. To the reaction mixture was added 600 mL of a lactose.phosphate buffer (an aqueous solution obtained by dissolving in 600 mL of distilled water for injection 100 g of lactose monohydrate, 0.45 g of $Na_2HPO_4.7H_2O$ and 0.35 g of $NaH_2PO_4.H_2O$). After stirring by a stirrer, a proper amount of distilled water for injection was added to adjust the total amount to 1 L. The medicament solution thus obtained was filtered through a 0.22 μm filter. Then, 5.3 ml portions of the filtrate were pipetted into vials, followed by freeze-drying. To each of the vials containing the freeze-dried injection preparation, 5 mL of distilled water for injection was added to thaw the preparation. The evaluation results of the pharmacokinetic parameter (AUC) of a rat, particle diameter, and membrane fluidity (order parameter (S), fluorescence anisotropy r, fluorescence polarity P) are shown in Table 2.

TABLE 2

Physicochemical parameters of an injection preparation containing a lipid A analog (500 μg/vial) and AUC (0–2 hr) of a rat administered with the preparation

| Example | Concentration (M) of NaOH in the dissolving step | Dispersing method | AUC (0–2 hr) (ng · hr/ml) | Particle diameter (nm) | fluorescence anisotropy (r) | fluorescence polarity (p) | Order parameter (S) |
|---|---|---|---|---|---|---|---|
| Ex 11 | 0.01 | Stirring under heat   | 2762 | 33.0 ± 9.9  | 0.215 | 0.291 | 0.735 |
| Ex 12 | 0.01 | Stirring under heat   | 1130 | 40.1 ± 13.0 | 0.23  | 0.310 | 0.760 |
| Ex 13 | 0.01 | Stirring under heat   | 624  | 60.9 ± 16.9 | 0.242 | 0.324 | 0.780 |
| Ex 14 | 0.01 | Stirring under heat   | 2007 | 30.7 ± 11.3 | 0.201 | 0.274 | 0.711 |
| Ex 15 | 0.01 | Stirring under heat   | 5921 | 18.0 ± 10.9 | 0.151 | 0.210 | 0.616 |
| Ex 16 | 0.01 | Stirring under heat   | 359  | 32.6 ± 13.2 | 0.237 | 0.318 | 0.772 |
| Ex 17 | 0.01 | Ultrasonic dispersion | 5300 | 16.8 ± 5.3  | 0.178 | 0.245 | 0.669 |
| Ex 18 | 0.01 | Ultrasonic dispersion | 2211 | 18.1 ± 5.2  | 0.203 | 0.276 | 0.714 |
| Ex 19 | 0.01 | Ultrasonic dispersion | 2229 | 16.1 ± 6.4  | 0.209 | 0.284 | 0.725 |
| Ex 20 | 0.01 | Ultrasonic dispersion | 2327 | 17.0 ± 5.1  | 0.193 | 0.264 | 0.696 |
| Ex 21 | 0.01 | Ultrasonic dispersion | 2386 | 34.6 ± 11.9 | 0.213 | 0.289 | 0.732 | particle diameter: average ± S.D.

Examples 11 and 16

In a glass beaker, 100 mg of the lipid A analog represented by the formula (III) was weighed, followed by the addition of 50 mL of 0.01M NaOH. The resulting mixture was stirred by a stirrer at room temperature (about 25° C.). To the reaction mixture was added 600 mL of a lactose.phosphate buffer (an aqueous solution obtained by dissolving in 600 mL of distilled water for injection 100 g of lactose monohydrate, 0.45 g of $Na_2HPO_4.7H_2O$ and 0.35 g of $NaH_2PO_4.H_2O$). After stirring by a stirrer, a proper amount of distilled water for injection was added to adjust the total amount to 1 L. The medicament solution thus obtained was filtered through a 0.22 μm filter. Then, 5.3 ml portions of the filtrate were pipetted into vials, followed by freeze-drying. To each of the vials containing the freeze-dried injection preparation, 5 ml of distilled water for injection was added to thaw the preparation. The evaluation results of the pharmacokinetic parameter (AUC) of a rat, particle size, and Example 22 to 26

In a glass beaker, 100 mg of the lipid A analog represented by the formula (III) was weighed. After addition of 50 mL of 0.003M NaOH, the resulting mixtures were stirred at 50±5° C. for 3, 8, 15, 30 and 90 minutes, respectively. To each of the reaction mixtures, 600 mL of a lactose.phosphate buffer (an aqueous solution obtained by dissolving in 600 mL of distilled water for injection 100 g of lactose monohydrate, 0.45 g of $Na_2HPO_4.7H_2O$ and 0.35 g of $NaH_2PO_4.H_2O$) was added. After stirring by a stirrer, a proper amount of distilled water for injection was added to adjust the total amount to 1 L. The medicament solution thus obtained was filtered through a 0.22 μm filter. Then, 5.3 ml portions of the filtrate were pipetted into vials, followed by freeze-drying. To each of the vials containing freeze-dried injection preparation, 5 ml of distilled water for injection was added to thaw the preparation. The evaluation results of the pharmacokinetic parameter (AUC) of a rat, particle diameter, membrane fluidity (order parameter (S)) and surface charge are shown in Table 3. Since stirring was conducted in a sodium hydroxide solution at a temperature (50±5° C.) not less than the phase transfer temperature (about 30° C.) of the lipid A analog represented by the formula (III), AUC depended on the stirring time and the longer the stirring time, the greater AUC. It has also been recognized that the greater AUC, the smaller order parameter (S). Between AUC and the particle diameter or surface charge, no definite correlation was recognized.

TABLE 3

Influence of stirring time in sodium hydroxide on physicochemical parameters of an injection preparation containing a lipid A analog (500 μg/vial) and on AUC (0–2 hr) of a rat administered with the preparation

| Example | Stirring time (min) in 0.003M NaOH | Dispersing method | AUC (0–2 hr) (ng · hr/ml) | Particle diameter (nm) | Surface charge (zeta potential: mV) | Order parameter (S) |
| --- | --- | --- | --- | --- | --- | --- |
| Ex 22 | 3 | stirring under heat | 1362 | 29.0 ± 14.0 | 0.215 | 0.759 |
| Ex 23 | 8 | stirring under heat | 5668 | 18.4 ± 6.8 | 0.23 | 0.721 |
| Ex 24 | 15 | stirring under heat | 7333 | 16.5 ± 6.0 | 0.242 | 0.695 |
| Ex 25 | 30 | stirring under heat | 8051 | 15.3 ± 5.0 | 0.201 | 0.661 |
| Ex 26 | 90 | stirring under heat | 9381 | 16.7 ± 5.3 | 0.151 | 0.636 | particle diameter: Mean ± S.D.

Example 27

In a glass beaker, 100 mg of the lipid A analog represented by the formula (III) was weighed, followed by the addition of 50 mL of 0.003M NaOH. The resulting mixture was stirred by a stirrer at 50±5° C. for 30 minutes. To the reaction mixture was added 600 mL of a lactose.phosphate (an aqueous solution obtained by dissolving in 600 mL of distilled water for injection 100 g of lactose monohydrate, 0.45 g of $Na_2HPO_4.7H_2O$ and 0.35 g of $NaH_2PO_4.H_2O$). After stirring by a stirrer, a proper amount of distilled water for injection was added to adjust the total amount to 1 L. The resulting medicament solution was filtered through a 0.22 μm filter. Each of 5.3 ml portions of the filtrate was pipetted into a vial and then freeze-dried. The initial stage product and products tested for stability under the conditions of 40° C. and 75% RH (freeze-dried injection preparations stored for 1, 2 and 3 months) were thawed with 5 ml of distilled water for injection with the replicate of 3 and their membrane fluidity (order parameter (S)) was evaluated. The results are shown in Table 4. Variations in the order parameter (S) were small upon measurement, indicating that the reproducibility was sufficient. In addition, it was revealed that the injection preparations, whether they were initial stage products or stored for 3 months, were stable free from variations in order parameter (S) and pharmacokinetic parameter.

TABLE 4

Change and reproducibility in order parameter (S) upon stability test of an injection preparation containing a lipid A analog (500 μg/vial)

| Measurement n | Initial | 1M (40° C.- 75% R.H.) | 2M (40° C.- 75% R.H.) | 3M (40° C.- 75% R.H.) |
| --- | --- | --- | --- | --- |
| 1 | 0.560 | 0.589 | 0.572 | 0.597 |
| 2 | 0.586 | 0.565 | 0.589 | 0.576 |
| 3 | 0.599 | 0.599 | 0.591 | 0.591 |
| Mean | 0.584 | 0.584 | 0.588 | 0.588 |
| CV (%) | 3.40 | 2.99 | 1.78 | 1.84 |

What is claimed is:

1. A method of forecasting a pharmacokinetic parameter of a lipid A analog as an aggregate structure in solution or in an injection preparation, wherein said aggregate structure in solution or injection preparation contains a lipid A analog or a pharmacologically acceptable salt thereof, said method comprising measuring at least one of membrane fluidity and circular dichroism of the solution or the injection preparation;

preparing a plurality of lots of solutions, each solution having a unique, known value of said pharmacokinetic parameter;

measuring the membrane fluidity or circular dichroism of said plurality of lots of solutions;

preparing a graphical correlation for said plurality of lots of solutions, said correlation being between the membrane fluidity or circular dichroism and said unique, known value of said pharmacokinetic parameter.

2. The method according to claim 1, wherein quality evaluation is conducted in order to obtain an injection preparation exhibiting a constant pharmacokinetic parameter.

3. The method according to claim 1, which is conducted during preparation of the injection preparation.

4. The method according to claim 1, wherein the membrane fluidity is measured by a fluorescence probe method which uses, as parameters, at least one of order parameter (S), fluorescence polarity (P) and fluorescence anisotropy (r).

5. The method according to claim 1, wherein the injection preparation further contains aggregates having a diameter not greater than 30 nm, and is prepared by dissolving the lipid A analog or a pharmacologically acceptable salt thereof in an alkaline aqueous solution and then adding a buffer thereto.

6. The method according to claim 1, wherein the injection preparation is an aqueous injection or freeze-dried preparation.

7. The method according to claim 1, wherein the lipid A analog or a pharmacologically acceptable salt thereof is a compound represented by the following formula (I):

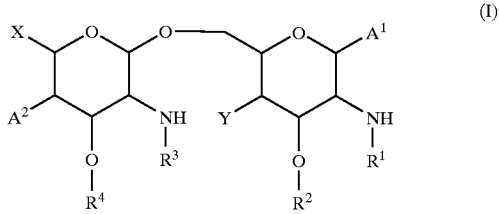

wherein at least one of $R^1$, $R^2$, $R^3$ and $R^4$ is

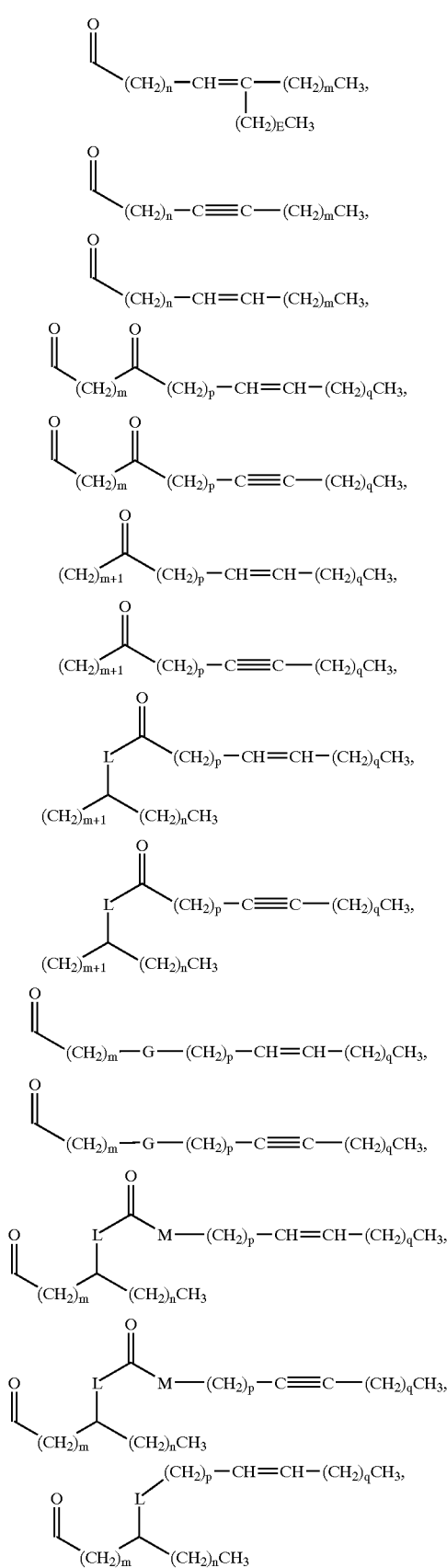

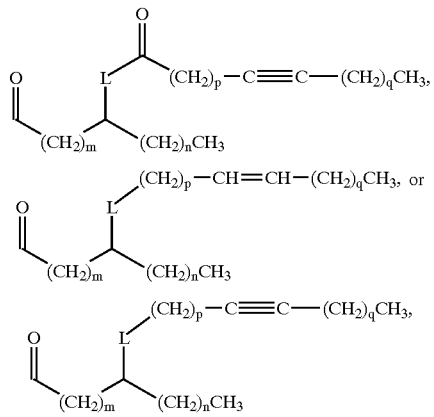

wherein each L is O, N or C; each M is O or N; each E independently is an integer of 0 to 14; each G independently is N, O, S, SO or $SO_2$; each m independently is an integer of 0 to 14; each n independently is an integer of 0 to 14; each p independently is an integer of 0 to 10; each q independently is an integer of 0 to 10, the rest of $R^1$, $R^2$, $R^3$ and $R^4$ are, independently of one another,

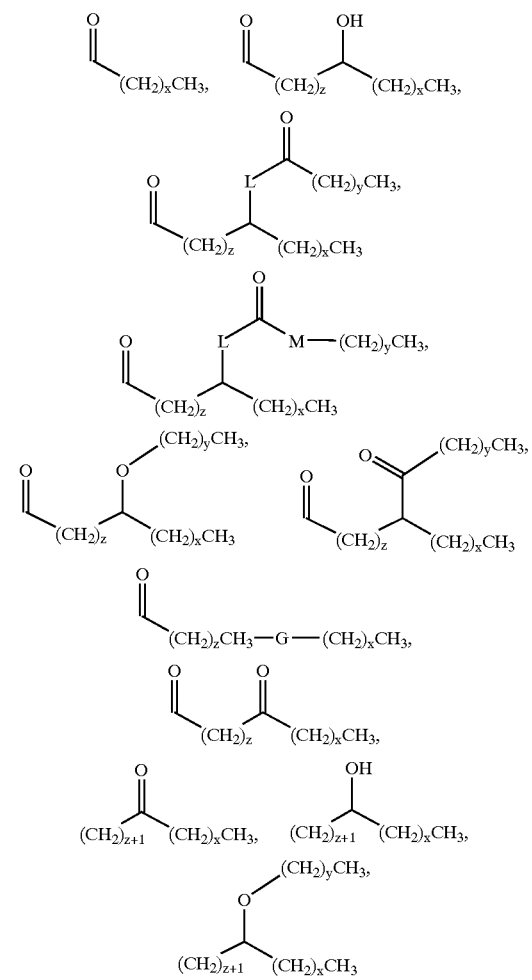

-continued

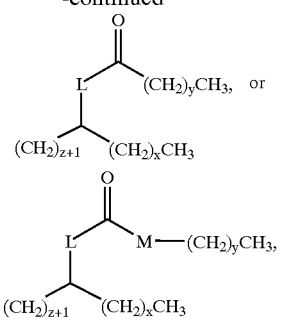

wherein each L is O, N or C; each M is O or N; each x independently is an integer of 0 to 14; each y independently is an integer of 0 to 14; each z independently is an integer of 0 to 10; each G independently is N, O, S, SO or $SO_2$, $A^1$ and $A^2$ are, independently of one another, H, OH, $OCH_3$,

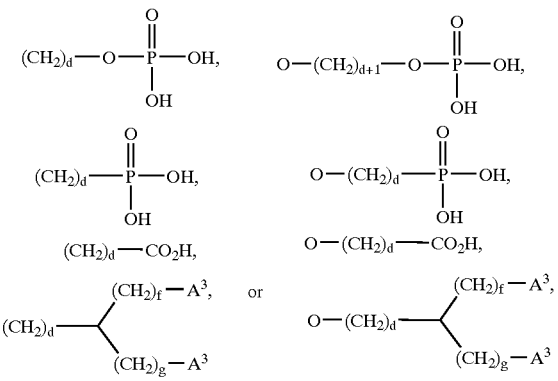

wherein each d independently is an integer of 0 to 5; each f independently is an integer of 0 to 5; each g independently is an integer of 0 to 5; each $A^3$ independently is

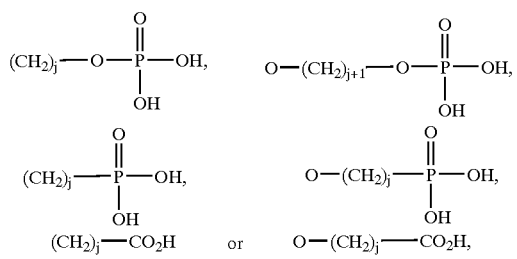

wherein each j independently is an integer of 0 to 14, X is H, $(CH_3)_tCH_3$, $(CH_2)_tOH$, $(CH_2)_tO(CH_2)_vCH_3$, $(CH_2)_tOPO(OH)_2$, $(CH_2)_t$—CH=CH—$(CH_2)_vCH_3$, $(CH_2)_t$—O—$R^5$,

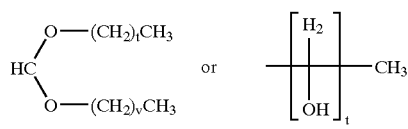

wherein t and v, are independently of one another, an integer of 0 to 14; $R^5$ is any of the above definitions of $R^1$ to $R^4$, Y is H, OH, $O(CH_2)_wCH_3$, a halogen atom,

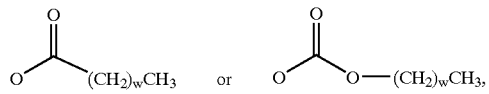

wherein w is an integer of 0 to 14,
or a pharmacologically acceptable salt thereof.

8. The method according to claim 1, wherein the lipid A analog is a compound represented by the following formula (II).

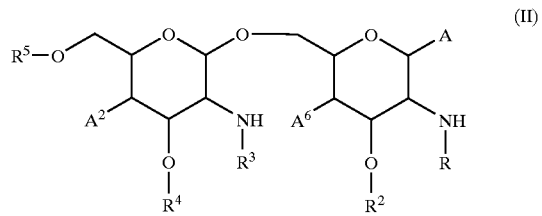

wherein $R^1$ is a group selected from the groups consisting of

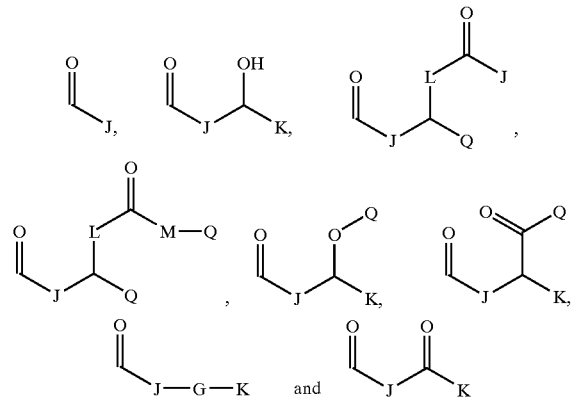

wherein J, K and Q are each a linear or branched alkyl group of 1 to 15 carbon atoms; L is O, $NH_2$ or $CH_2$; M is O or NH; G is NH, O, S, SO or $SO_2$,
$R^2$ is a linear or branched alkyl group of 5 to 15 carbon atoms, $R^3$ is a group selected from the groups consisting of

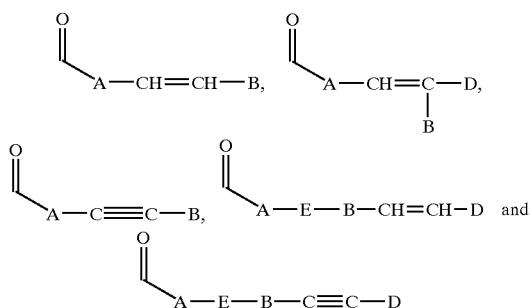

wherein E is N, O, S, SO or $SO_2$; A, B and D are each a linear or branched alkyl group of 1 to 15 carbon atoms, $R^4$ is a group selected from the groups consisting of a linear or branched alkyl group of 4 to 20 carbon atoms and

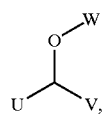

wherein U and V are each a linear or branched alkyl group of 2 to 15 carbon atoms; W is a hydrogen atom or a linear or branched alkyl group of 1 to 5 carbon atoms, $R^5$ is a group selected from the groups consisting of a hydrogen atom, J', —J'—OH, —J'—O—K', —J'—O—K'—OH and —J'—O—PO(OH)$_2$, wherein J' and K' are each a linear or branched alkyl group of 1 to 5 carbon atoms, $R^6$ is a group selected from the groups consisting of a hydroxyl group, a halogen atom, an alkoxy group of 1 to 5 carbon atoms, and an acyloxy group of 1 to 5 carbon atoms, $A^1$ and $A^2$ independently are each a group selected from the groups consisting of

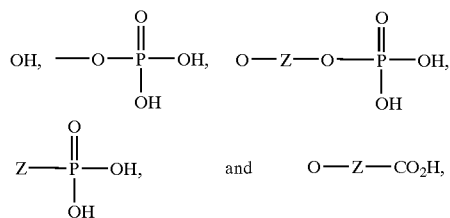

wherein Z is a linear or branched alkyl group of 1 to 10 carbon atoms, or a pharmacologically acceptable salt thereof.

9. The method according to claim 1, wherein the lipid A analog is a compound represented by the following formula (III):

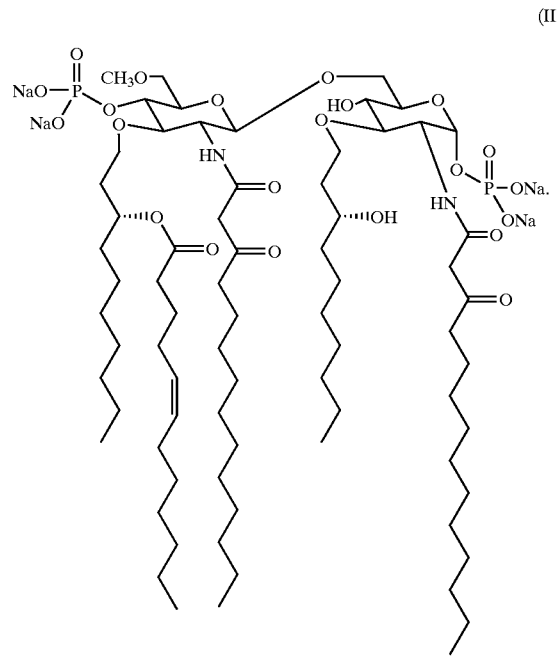

10. The method according to claim 1, wherein the lipid A analog is a compound represented by the following formula (IV):

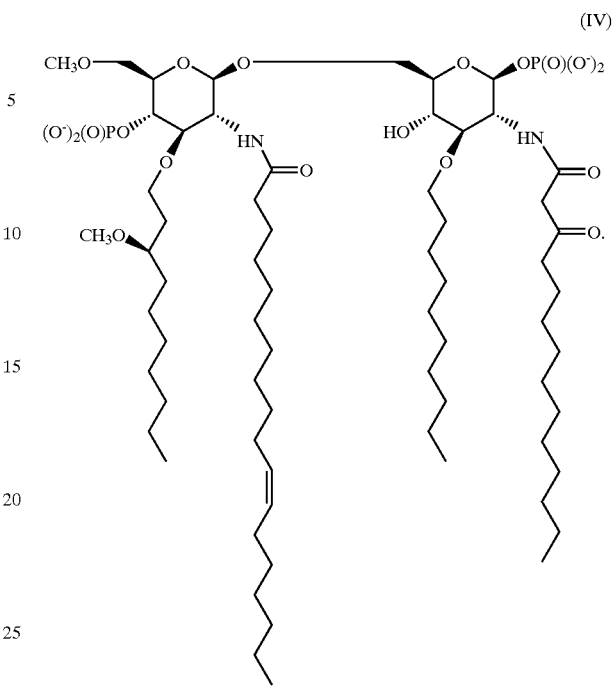

11. The method according to claim 1, wherein the lipid A analog or a pharmacologically acceptable salt thereof has an aggregate structure in endoplasmic reticulum of lipid biomolecular membrane or micelle.

12. A method of forecasting a pharmacokinetic parameter of a lipid A analog as an aggregate structure in solution or in an injection preparation, wherein said aggregate structure in solution or injection preparation contains a lipid A analog or a pharmacologically acceptable salt thereof, said method comprising measuring at least one of membrane fluidity and circular dichroism of the solution or the injection preparation;

preparing a plurality of lots of solutions, each solution having a unique, known value of said membrane fluidity or circular dichroism;

measuring the pharmacokinetic parameter of said plurality of lots of solutions;

preparing a graphical correlation for said plurality of lots of solutions, said correlation being between the pharmacokinetic parameter and said unique, known value of membrane fluidity or circular dichroism.

13. The method according to claim 12, wherein quality evaluation is conducted in order to obtain an injection preparation exhibiting a constant pharmacokinetic parameter.

14. The method according to claim 12, which is conducted during preparation of the injection preparation.

15. The method according to claim 12, wherein the membrane fluidity is measured by a fluorescence probe method which uses, as parameters, at least one of order parameter (S), fluorescence polarity (P) and fluorescence anisotropy (r).

16. The method according to claim 12, wherein the injection preparation further contains aggregates having a diameter not greater than 30 nm, and is prepared by dissolving the lipid A analog or a pharmacologically acceptable salt thereof in an alkaline aqueous solution and then adding a buffer thereto.

17. The method according to claim 12, wherein the injection preparation is an aqueous injection or freeze-dried preparation.

18. The method according to claim 12, wherein the lipid A analog or a pharmacologically acceptable salt thereof is a compound represented by the following formula (I):

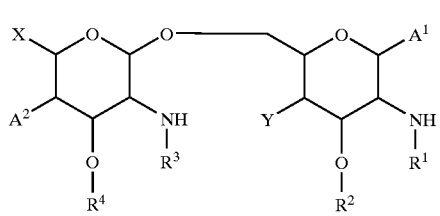

wherein at least one of $R^1$, $R^2$, $R^3$ and $R^4$ is

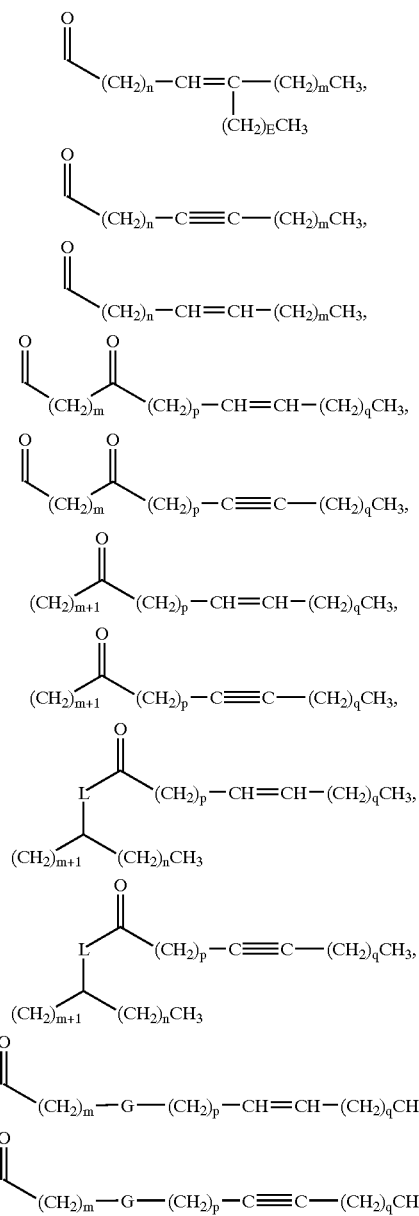

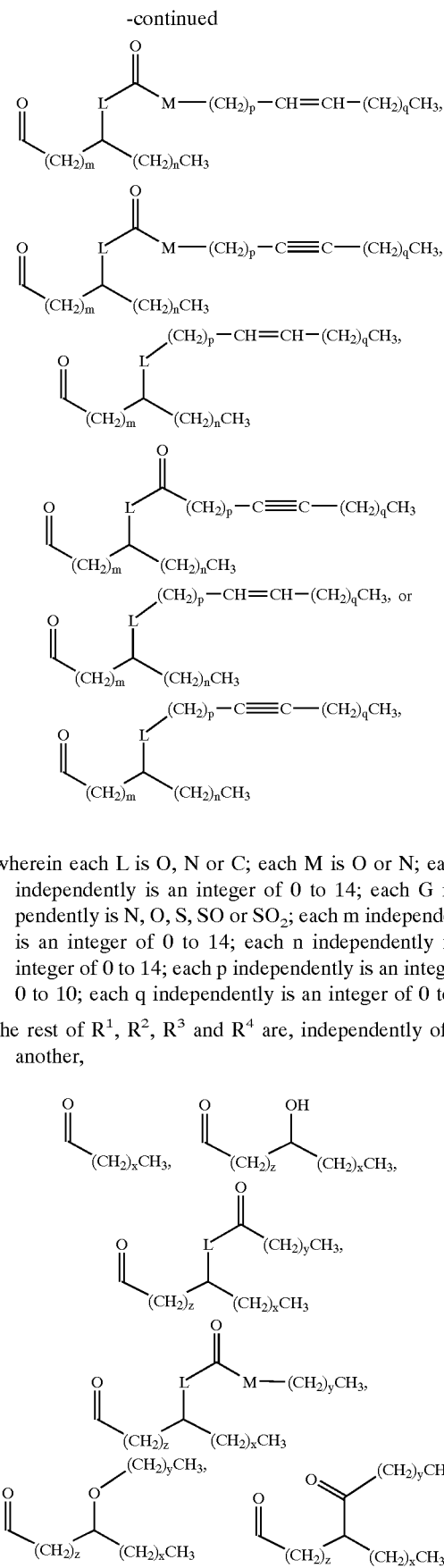

wherein each L is O, N or C; each M is O or N; each E independently is an integer of 0 to 14; each G independently is N, O, S, SO or $SO_2$; each m independently is an integer of 0 to 14; each n independently is an integer of 0 to 14; each p independently is an integer of 0 to 10; each q independently is an integer of 0 to 10, the rest of $R^1$, $R^2$, $R^3$ and $R^4$ are, independently of one another,

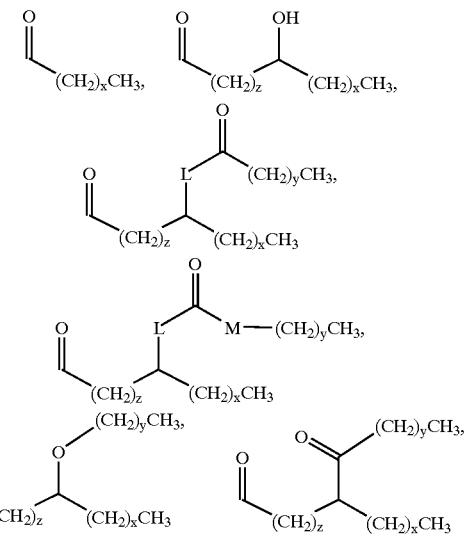

-continued

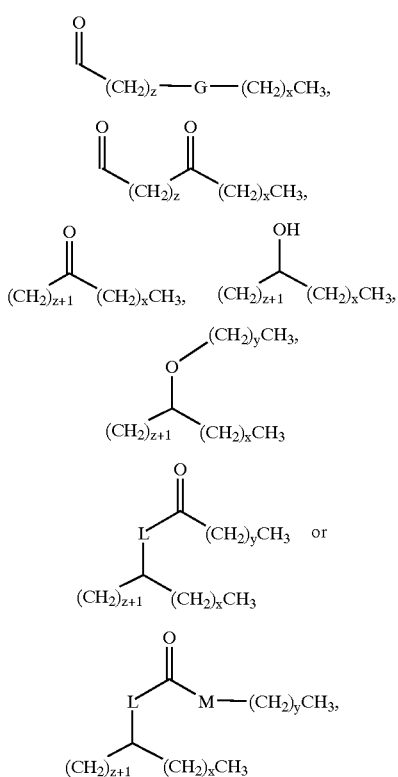

wherein each L is O, N or C; each M is O or N; each x independently is an integer of 0 to 14; each y independently is an integer of 0 to 14; each 2 independently is an integer of 0 to 10; each G independently is N, O, S, SO or $SO_2$, $A^1$ and $A^2$ are, independently of one another, H, OH, $OCH_3$,

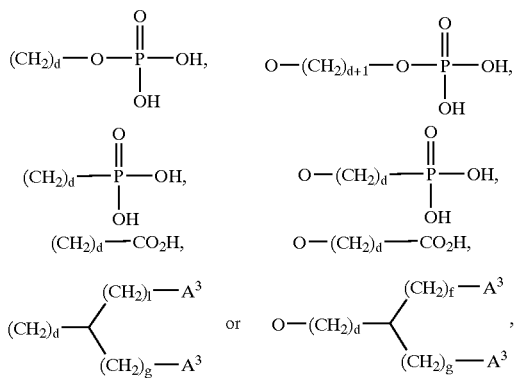

wherein each d independently is an integer of 0 to 5; each f independently is an integer of 0 to 5; each g independently is an integer of 0 to 5; each $A^3$ independently is

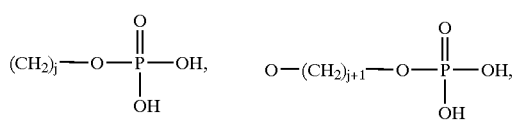

-continued

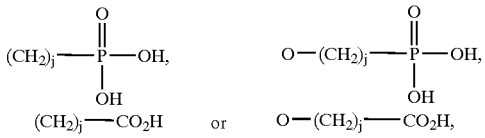

wherein each j independently is an integer of 0 to 14, X is H, $(CH_2)_tCH_3$, $(CH_2)_tOH$, $(CH_2)_tO(CH_2)_vCH_3$, $(CH_2)_tOPO(OH)_2$, $(CH_2)_t$—CH=CH—$(CH_2)_vCH_3$, $(CH_2)_t$—O—$R^5$,

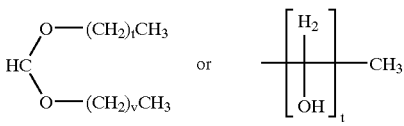

wherein t and v, are independently of one another, an integer of 0 to 14; $R^5$ is any of the above definitions of $R^1$ to $R^4$, Y is H, OH, $O(CH_2)_wCH_3$, a halogen atom,

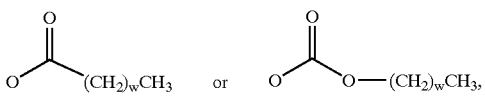

wherein w is an integer of 0 to 14,
or a pharmacologically acceptable salt thereof.

19. The method according to claim 12, wherein the lipid A analog is a compound represented by the following formula (II):

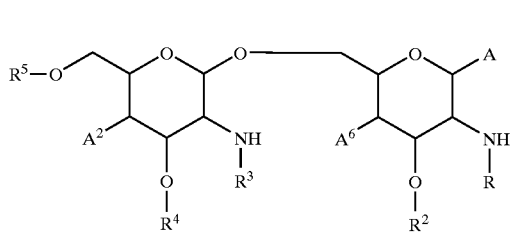

wherein $R^1$ is a group selected from the groups consisting of

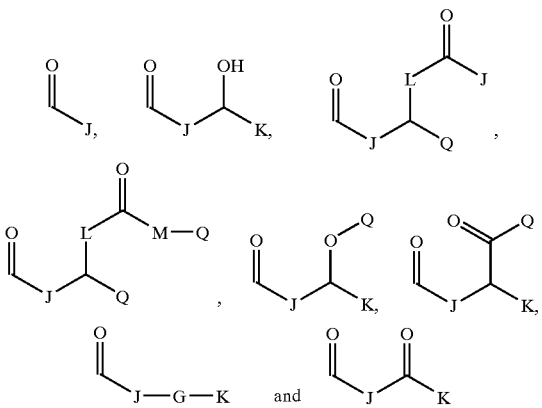

wherein J, K and Q are each a linear or branched alkyl group of 1 to 15 carbon atoms; L is O, $NH_2$ or $CH_2$; M is O or NH; G is NH, O, S, SO or $S_2$, $R^2$ is a linear or branched alkyl group of 5 to 15 carbon atoms, $R^3$ is a group selected from the groups consisting of

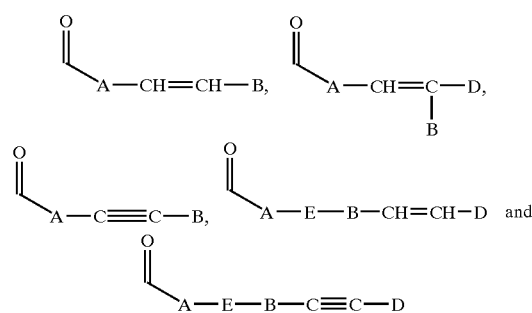

wherein E is N, O, S, SO or $SO_2$; A, B and D are each a linear or branched alkyl group of 1 to 15 carbon atoms, $R^4$ is a group selected from the groups consisting of a linear or branched alkyl group of 4 to 20 carbon atoms and

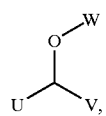

wherein U and V are each a linear or branched alkyl group of 2 to 15 carbon atoms; W is a hydrogen atom or a linear or branched alkyl group of 1 to 5 carbon atoms, $R^5$ is a group selected from the groups consisting of a hydrogen atom, J', —J'—OH, —J'—O—K', —J'—O—K'—OH and —J'—O—$PO(OH)_2$, wherein J' and K' are each a linear or branched alkyl group of 1 to 5 carbon atoms, $R^6$ is a group selected from the groups consisting of a hydroxyl group, a halogen atom, an alkoxy group of 1 to 5 carbon atoms, and an acyloxy group of 1 to 5 carbon atoms, $A^1$ and $A^2$ independently are each a group selected from the groups consisting of

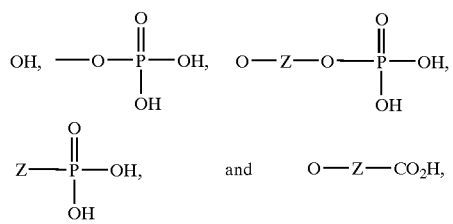

wherein Z is a linear or branched alkyl group of 1 to 10 carbon atoms, or a pharmacologically acceptable salt thereof.

20. The method according to claim 12, wherein the lipid A analog is a compound represented by the following formula (III):

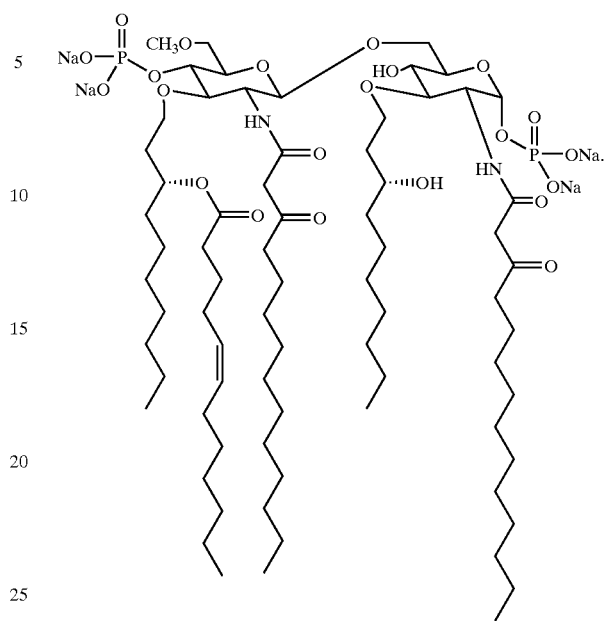

21. The method according to claim 12, wherein the lipid A analog is a compound represented by the following formula (IV):

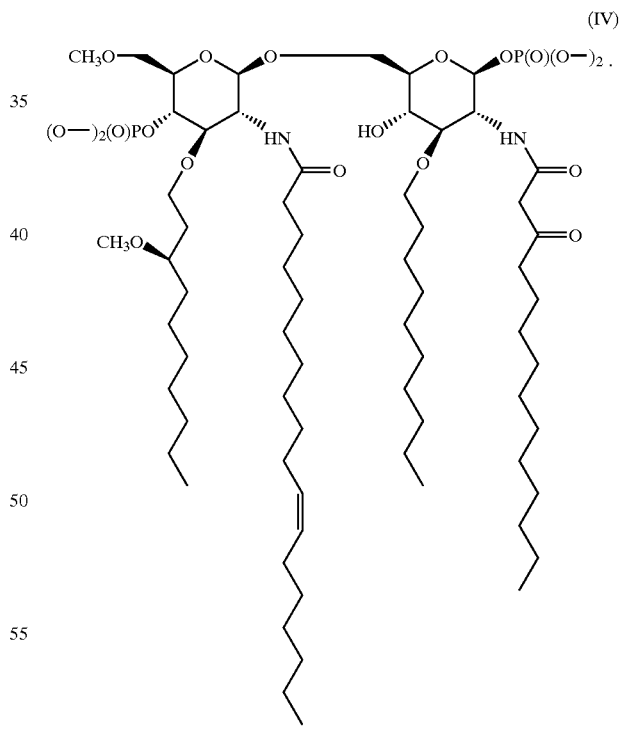

22. The method according to claim 12, wherein the lipid A analog or a pharmacologically acceptable salt thereof has an aggregate structure in endoplasmic reticulum of lipid biomolecular membrane or micelle.

* * * * *

UNITED STATES PATENT AND TRADEMARK OFFICE
CERTIFICATE OF CORRECTION

PATENT NO. : 6,828,155 B1  
APPLICATION NO. : 09/786060  
DATED : December 7, 2004  
INVENTOR(S) : Kazuhiro Kaneko et al.

It is certified that error appears in the above-identified patent and that said Letters Patent is hereby corrected as shown below:

IN THE CLAIMS:

Claim 8, Column 26, Line 12:

Replace "(II)." with --(II):--

Signed and Sealed this

Eleventh Day of December, 2007

JON W. DUDAS  
*Director of the United States Patent and Trademark Office*

UNITED STATES PATENT AND TRADEMARK OFFICE
CERTIFICATE OF CORRECTION

PATENT NO.       : 6,828,155 B1
APPLICATION NO.  : 09/786060
DATED            : December 7, 2004
INVENTOR(S)      : Kazuhiro Kaneko et al.

It is certified that error appears in the above-identified patent and that said Letters Patent is hereby corrected as shown below:

Claim 8, Column 26, Lines 13-22:

Replace the following formula:

"
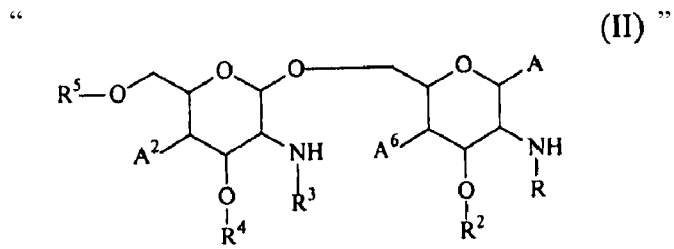
(II) "

With:

--
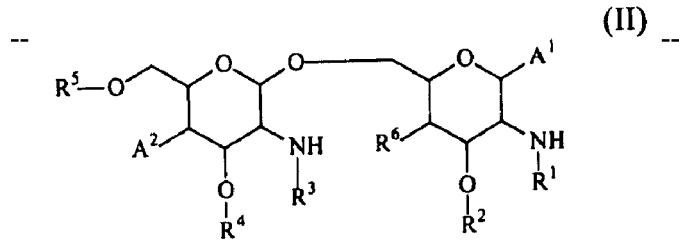
(II) --

UNITED STATES PATENT AND TRADEMARK OFFICE
CERTIFICATE OF CORRECTION

PATENT NO. : 6,828,155 B1
APPLICATION NO. : 09/786060
DATED : December 7, 2004
INVENTOR(S) : Kazuhiro Kaneko et al.

It is certified that error appears in the above-identified patent and that said Letters Patent is hereby corrected as shown below:

Claim 19, Column 32, Lines 35-44:

Replace the following formula:

"
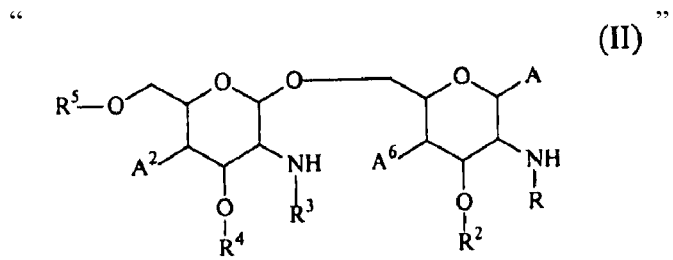
(II)"

With:

--
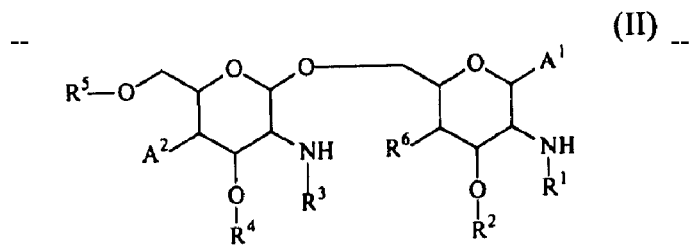
(II) --

Signed and Sealed this

Twenty-fourth Day of June, 2008

JON W. DUDAS
*Director of the United States Patent and Trademark Office*